(12) United States Patent
Phillips et al.

(10) Patent No.: US 7,985,888 B2
(45) Date of Patent: Jul. 26, 2011

(54) METHOD FOR INCREASING SEED SIZE BY INCREASING GIBBERELLIN CONTENT IN THE SEEDS

(75) Inventors: Andrew Leonard Phillips, Harpenden (GB); Peter Hedden, Harpenden (GB); John Robert Lenton, Bristol (GB); Daniel James Evans, Wales (GB); Rebecca Stratford, Cambridge (GB)

(73) Assignee: Rothamsted Research Limited, Harpenden, Hertfordshire (GB)

( * ) Notice: Subject to any disclaimer, the term of this patent is extended or adjusted under 35 U.S.C. 154(b) by 678 days.

(21) Appl. No.: 11/575,892

(22) PCT Filed: Sep. 23, 2005

(86) PCT No.: PCT/GB2005/003691
§ 371 (c)(1),
(2), (4) Date: Apr. 16, 2008

(87) PCT Pub. No.: WO2006/032916
PCT Pub. Date: Mar. 30, 2006

(65) Prior Publication Data
US 2009/0007295 A1    Jan. 1, 2009

(30) Foreign Application Priority Data
Sep. 23, 2004   (GB) .................................. 0421241.1

(51) Int. Cl.
*A01H 1/00*    (2006.01)
*A01H 5/00*    (2006.01)
*A01H 5/10*    (2006.01)
(52) U.S. Cl. .......... 800/278; 800/295; 435/410; 435/468
(58) Field of Classification Search .................... None
See application file for complete search history.

(56) References Cited

U.S. PATENT DOCUMENTS

| | | | |
|---|---|---|---|
| 6,670,527 | B1 | 12/2003 | Thomas et al. |
| 7,262,340 | B2 | 8/2007 | Thomas et al. |
| 2004/0121321 | A1 | 6/2004 | Brown et al. |

FOREIGN PATENT DOCUMENTS

| | | |
|---|---|---|
| WO | WO 94/28141 A1 | 12/1994 |
| WO | WO 99/66029 A2 | 12/1999 |
| WO | WO 00/09722 A2 | 2/2000 |

OTHER PUBLICATIONS

Barcelo, P. and Lazzeri, P.A., "Transformation of Cereals by Microprojectile Bombardment of Immature Inflorescence and Scutellum Tissues," in *Plant Gene Transfer and Expression Protocols*, Jones, H., eds., Humana Press Inc., Totowa, New Jersey, pp. 113-123 (1995).

Chiang, H.-H., et al., "Isolation of the *Arabidopsis GA4* Locus," *The Plant Cell* 7:195-201, American Society of Plant Physiologists (1995).

Christensen, A.H. and Quail, P.H., "Ubiquitin promoter-based vectors for high-level expression of selectable and/or screenable marker genes in monocotyledonous plants," *Transgenic Research* 5:213-218, Chapman & Hall(1996).

Coles, J.P., et al., "Modification of gibberellin production and plant development in *Arabidopsis* by sense and antisense expression of gibberellin 20-oxidase genes," *The Plant Journal* 17:547-556, Blackwell Science Ltd. (1999).

Green, L.S., et al., "Grain Development Mutants of Barley (α-Amylase Production during Grain Maturation and Its Relation to Endogenous Gibberellic Acid Content)," *Plant Physiol.* 114: 203-212, American Society of Plant Biologists (1997).

Hedden, P. and Kamiya, Y., "Gibberellin Biosynthesis: Enzymes, Genes and Their Regulation," *Annu. Rev. Plant Physiol. Plant Mol. Biol.* 48:431-460, Annual Reviews Inc. (1997).

Huang, S., et al., "Overexpression of 20-Oxidase Confers a Gibberellin-Overproduction Phenotype in *Arabidopsis*," *Plant Physiol.* 118:773-781, American Society of Plant Biologists (1998).

Lamacchia, C., et al., "Endosperm-specific activity of a storage protein gene promoter in transgenic wheat seed," *Journal of Experimental Botany* 52:243-250, Society for Experimental Biology (2001).

Pastori, G.M., et al., "Age-dependent transformation frequency in elite wheat varieties," *Journal of Experimental Botany* 52:857-863, Society for Experimental Biology (2001).

Phillips, A.L., et al., "Isolation and Expression of Three Gibberellin 20-Oxidase cDNA Clones from *Arabidopsis*," *Plant Physiol.* 108:1049-1057, American Society of Plant Biologists (1995).

Rasco-Gaunt, S., et al., "Procedures allowing the transformation of a range of European elite wheat (*Triticum aestivum* L.) varieties via particle bombardment," *Journal of Experimental Botany* 52:865-874, Society for experimental Biology (2001).

Singh, D.P., et al., "Gibberellins Are Required for Seed Development and Pollen Tube Growth in *Arabidopsis*," *The Plant Cell* 14:3133-3147, American Society of Plant Biologists (2002).

Sparks, C.A. and Jones, H.D., "Transformation of Wheat by Biolistics," Chapter 2 in: *Transgenic Crops of the World. Essential Protocols*, Curtis, I.S., eds., Kluwer Academic Publishers, Dordrecht, The Netherlands, pp. 19-34 (2004).

Swain, S.M., et al., "Gibberellins are required for embryo growth and seed development in pea," *The Plant Journal* 12:1329-1338, Blackwell Publishing (1997).

Tudzynski, B., et al., "Characterization of the Final Two Genes of the Gibberellin Biosynthesis Gene Cluster of *Gibberella fujikuroi: des* and *P450-3* Encode $GA_4$ Desaturase and the 13-Hydroxylase, Respectively," *The Journal of Biological Chemistry* 278:28635-28643, The American Society for Biochemistry and Molecular Biology, Inc. (Aug. 2003).

Communication dated May 28, 2008, from the European Patent Office, regarding corresponding EPO application No. 05 786 335.9-2403 (4 pages).

*Primary Examiner* — Eileen B O'Hara
(74) *Attorney, Agent, or Firm* — Sterne, Kessler, Goldstein & Fox P.L.L.C.

(57) ABSTRACT

A method is provided for increasing the weight of plant seed, which comprises preparing a genetically modified plant in which gibberellin content has been manipulated in the seed of the plant.

21 Claims, 7 Drawing Sheets

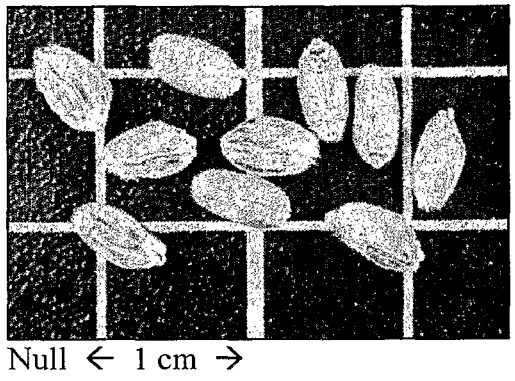
Null ← 1 cm →
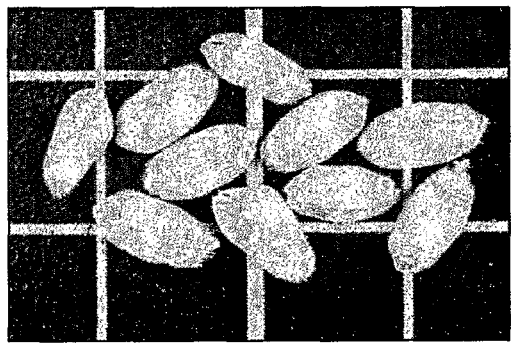
T45-2-8
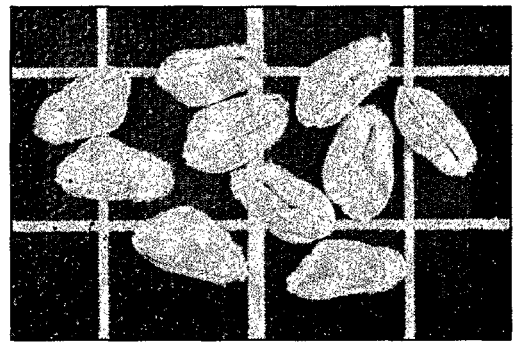
T45-3-7
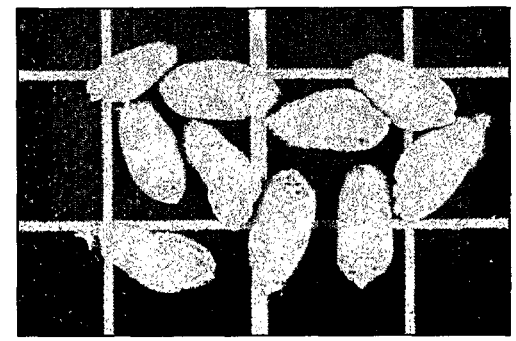
T45-4-19
T45-5-18
FIG. 2

```
   1    TTAATTAAAA ATATGCAACA TAATTTCCTT TTTACTTGGC TAATTATATT
  51    TGATAAATAT TTCACAGATA TACAATAATC AAACACAATA AATCATATGT
 101    GTTTTTAGTT TTAGTTCTCA TATCCAAATA TACAATAGCT AACCAAATCT
 151    CATCGGGAAG TTAGCCATGC CGAGGTAGGT TGTTGCCGGA ATGTTTTTAG
 201    TTTTAGTTCT CATACAACCA AATCTCATTC AAATATATAA AACATTCCGG
 251    CAACAACTTG TGGCGTACAT CTAGTTACAA GGGAATATTA GTGATGGCGT
 301    GAGCAAGCGA TAAGGCCAAG GAGAGAAGAA GTGCATCGTC TACGGAGGCC
 351    AGGGAAAGAC AATGGACATG CAGAGAGGCA GGGGCGGGGA AGAAACACTT
 401    GGAGATCATA GAAGAAGATA AGAGGTTAAA CATAGGAGGA GGATATAATG
 451    GACAATTAAA TCTGCGTTAG TTGAACTCAT TTGGGAAGTA AACAAATTTT
 501    CTATTCTGTG TAAACCAAAC TATTTGACGC GGATTTTCTC TGAAGATCCT
 551    ATATTAATTT TAGACATGGT TTGGCTAGTT CATTTGTCGT GAAAAGGTGT
 601    TTCCATAAGT CCAAAATTCT ACCAACTTTT TTGTATGGCA CGTCATAGCA
 651    TAGATAGATG TTGTGAGTCA CTGGATAGAT ATTGTGAGTC ATAGCATGGA
 701    TTCGTGTTGC TGGAAATCCA ACTACATGAC AAGCAACAAA ACCTGAAATG
 751    GGCTTTAGGA GTTAACAATT TACTTGTTCC ATGCAGGCTA CCTTCCACTA
 801    CTCGACATGC TTAGAAGCTT TGAGTGGCCG TAGATTTGCA AAAGCAATGG
 851    CTAACAGACA CATATTCTGC CAAACCCCAA GAAGGATAAT CACTTTTCTT
 901    AGATAAAAAA GAACAGACCA ATATACAAAC ATCCACACTT CTGCAAACAA
 951    TACATCAGAA CTAGGATTAC GCCGATTACG TGGCTTTAGC AGACTGTCCA
1001    AAAATCTGTT TTGCAAAGCT CCAATTGCTC CTTGCTTATC CAGCTTCTTT
1051    TGTGTTGGCA AACTGCGCTT TTCCAACCGA TTTTGTTCTT CTCGCGCTTT
1101    CTTCTTAGGC TAAACAAACC TCACCGTGCA CGCAGCCATG GTCCTGAACC
1151    TTCACCTCGT CCCTATAAAA GCCTAGCCAA CCTTCACAAT CTTATCATCA
1201    CCCACAACAC CGAGCACCAC AAACTAGAGA TCAATTCACT GATAGTCCAC
1251    CAGGCCT
```

FIG. 3

```
   1    CTCGAGATGG CCGTAAGTTT CGTAACAACA TCTCCTGAGG AAGAAGACAA
  51    ACCGAAGCTA GGCCTTGGAA ATATTCAAAC TCCGTTAATC TTCAACCCTT
 101    CAATGCTTAA CCTTCAAGCC AATATCCCAA ACCAATTCAT CTGGCCTGAC
 151    GACGAAAAAC CTTCCATCAA CGTTCTCGAG CTTGATGTTC CTCTCATCGA
 201    CCTTCAAAAC CTTCTCTCTG ATCCATCCTC CACTTTAGAT GCTTCGAGAC
 251    TGATCTCTGA GGCCTGTAAG AAGCACGGTT TCTTCCTCGT GGTCAATCAC
 301    GGCATCAGCG AGGAGCTTAT ATCAGACGCT CATGAATACA CGAGCCGCTT
 351    CTTTGATATG CCTCTCTCCG AAAAACAGAG GGTTCTTAGA AAATCCGGTG
 401    AGAGTGTTGG CTACGCAAGC AGTTTCACCG GACGCTTCTC CACCAAGCTT
 451    CCATGGAAGG AGACCCTTTC TTTCCGGTTT TGCGACGACA TGAGCCGCTC
 501    AAAATCCGTT CAAGATTACT CTGCGATGC GTTGGGACAT GGGTTTCAGC
 551    CATTTGGGAA GGTGTATCAA GAGTATTGTG AAGCAATGAG TTCTCTATCA
 601    TTGAAGATCA TGGAGCTTCT CGGGCTAAGT TTAGGCGTAA ACGGGACTA
 651    CTTTAGAGAG TTTTTCGAAG AAAACGATTC AATAATGAGA CTGAATTACT
 701    ACCCTCCATG TATAAAACCA GATCTCACAC TAGGAACAGG ACCTCATTGT
 751    GATCCAACAT CTCTTACCAT CCTTCACCAA GACCATGTTA ATGGCCTTCA
 801    AGTCTTTGTG GAAAATCAAT GGCGCTCCAT TCGTCCCAAC CCCAAGGCCT
 851    TTGTGGTCAA TATCGGCGAT ACTTTCATGG CTCTATCGAA CGATAGATAC
 901    AAGAGCTGCT TGCACCGGGC GGTGGTGAAC AGCAAGAGCG AGAGGAAGTC
 951    ACTTGCATTC TTCTTGTGTC CGAAAAAGA CAGAGTAGTG ACGCCACCGA
1001    GAGAGCTTTT GGACAGCATC ACATCAAGAA GATACCCTGA CTTACATGG
1051    TCTATGTTCC TTGAGTTCAC TCAGAAACAT TATAGAGCAG ACATGAACAC
1101    TCTCCAAGCC TTTTCAGATT GGCTCACCAA ACCCATCTAA GAGCTC
```

FIG. 4

```
  1    MAVSFVTTSP EEEDKPKLGL GNIQTPLIFN PSMLNLQANI PNQFIWPDDE
 51    KPSINVLELD VPLIDLQNLL SDPSSTLDAS RLISEACKKH GFFLVVNHGI
101    SEELISDAHE YTSRFFDMPL SEKQRVLRKS GESVGYASSF TGRFSTKLPW
151    KETLSFRFCD DMSRSKSVQD YFCDALGHGF QPFGKVYQEY CEAMSSLSLK
201    IMELLGLSLG VKRDYFREFF EENDSIMRLN YYPPCIKPDL TLGTGPHCDP
251    TSLTILHQDH VNGLQVFVEN QWRSIRPNPK AFVVNIGDTF MALSNDRYKS
301    CLHRAVVNSK SERKSLAFFL CPKKDRVVTP PRELLDSITS RRYPDFTWSM
351    FLEFTQKHYR ADMNTLQAFS DWLTKPI
```

FIG. 5

```
   1    ATGCCTGCTA TGTTAACAGA TGTGTTTAGA GGCCATCCCA TTCACCTCCC
  51    ACACTCTCAC ATACCTGACT TCACATCTCT CCGGGAGCTC CCGGATTCTT
 101    ACAAGTGGAC CCCTAAAGAC GATCTCCTCT TCTCCGCTGC TCCTTCTCCT
 151    CCGGCCACCG GTGAAAACAT CCCTCTCATC GACCTCGACC ACCCGGACGC
 201    GACTAACCAA ATCGGTCATG CATGTAGAAC TTGGGGTGCC TTCCAAATCT
 251    CAAACCACGG CGTGCCTTTG GGACTTCTCC AAGACATTGA GTTTCTCACC
 301    GGTAGTCTCT TCGGGCTACC TGTCCAACGC AAGCTTAAGT CTGCTCGGTC
 351    GGAGACAGGT GTGTCCGGCT ACGGCGTCGC TCGTATCGCA TCTTTCTTCA
 401    ATAAGCAAAT GTGGTCCGAA GGTTTCACCA TCACTGGCTC GCCTCTCAAC
 451    GATTTCCGTA AACTTTGGCC CCAACATCAC CTCAACTACT GCGATATCGT
 501    TGAAGAGTAC GAGGAACATA TGAAAAAGTT GGCATCGAAA TTGATGTGGT
 551    TAGCACTAAA TTCACTTGGG GTCAGCGAAG AAGACATTGA ATGGGCCAGT
 601    CTCAGTTCAG ATTTAAACTG GGCCCAAGCT GCTCTCCAGC TAAATCACTA
 651    CCCGGTTTGT CCTGAACCGG ACCGAGCCAT GGGTCTAGCA GCTCATACCG
 701    ACTCCACCCT CCTAACCATT CTGTACCAGA ACAATACCGC CGGTCTACAA
 751    GTATTTCGCG ATGATCTTGG TTGGGTCACC GTGCCACCGT TTCCTGGCTC
 801    GCTCGTGGTT AACGTTGGTG ACCTCTTCCA CATCCTATCC AATGGATTGT
 851    TTAAAAGCGT GTTGCACCGC GCTCGGGTTA ACCAAACCAG AGCCCGGTTA
 901    TCTGTAGCAT TCCTTTGGGG TCCGCAATCT GATATCAAGA TATCACCTGT
 951    ACCGAAGCTG GTTAGTCCCG TTGAATCGCC TCTATACCAA TCGGTGACAT
1001    GGAAAGAGTA TCTTCGAACA AAAGCAACTC ACTTCAACAA AGCTCTTTCA
1051    ATGATTAGAA ATCACAGAGA AGAATGA
```

FIG. 6

```
  1    MPAMLTDVFR GHPIHLPHSH IPDFTSLREL PDSYKWTPKD DLLFSAAPSP
 51    PATGENIPLI DLDHPDATNQ IGHACRTWGA FQISNHGVPL GLLQDIEFLT
101    GSLFGLPVQR KLKSARSETG VSGYGVARIA SFFNKQMWSE GFTITGSPLN
151    DFRKLWPQHH LNYCDIVEEY EEHMKKLASK LMWLALNSLG VSEEDIEWAS
201    LSSDLNWAQA ALQLNHYPVC PEPDRAMGLA AHTDSTLLTI LYQNNTAGLQ
251    VFRDDLGWVT VPPFPGSLVV NVGDLFHILS NGLFKSVLHR ARVNQTRARL
301    SVAFLWGPQS DIKISPVPKL VSPVESPLYQ SVTWKEYLRT KATHFNKALS
351    MIRNHREE
```

FIG. 7

```
   1   ATGCCTCATA AAGATAATCT TCTTGAATCG CCAGTGGGCA AGAGTGTCAC
  51   TGCTACTATA GCCTACCATA GCGGACCGGC TCTTCCAACC TCCCCGATCG
 101   CTGGTGTCAC TACGCTCCAA GACTGCACTC AGCAGGCCGT AGCAGTGACT
 151   GATATCCGCC CTTCAGTCTC GTCCTTTACC CTAGATGGTA ACGGCTTCCA
 201   GGTTGTCAAA CATACATCGG CGGTAGGCTC TCCGCCGTAT GATCACTCGT
 251   CGTGGACAGA TCCAGTCGTT CGCAAGGAAG TGTATGACCC CGAAATCATT
 301   GAACTGGCAA AGTCTCTCAC TGGAGCCAAG AAGGTCATGA TTCTACTTGC
 351   TTCGTCTCGG AATGTTCCCT TCAAGGAGCC AGAGCTCGCC CCTCCTTATC
 401   CCATGCCTGG CAAATCAAGC AGCGGCAGCA AGGAAAGGGA AGCCATCCCA
 451   GCTAATGAGC TCCCTACTAC AAGGGCAAAA GGTTTCCAAA AAGGCGAAGA
 501   GGAAGGCCCA GTACGAAAGC CTCATAAGGA CTGGGGTCCA TCCGGTGCGT
 551   GGAACACTCT CCGGAACTGG AGCCAAGAGC TCATTGATGA GGCTGGCGAT
 601   ATCATCAAGG CTGGCGATGA GGCTGCAAAG CTGCCAGGGG GCAGAGCAAA
 651   GAACTACCAA GGCAGACGAT GGGCCCTGTA TACTACCTGG CGTCCACTGA
 701   AAACTGTCAA GCGGGATCCC ATGGCCTATG TAGACTACTG GACAGCTGAT
 751   GAGGAAGATG GCGTGAGCTT CTGGCGTAAC CCGCCAGGGG TGCATGGGAC
 801   ATTTGAGTCG GATGTACTAC TTACCAAGGC TAATCCAAAG CATAAGTGGT
 851   ACTGGATCAG TGACCAGACT CCGGATGAGG TTCTCCTCAT GAAGATCATG
 901   GACACCGAGA GTGAGAAGGA CGGGAGTGAA ATAGCGGGAG GGGTTCACCA
 951   CTGTTCATTT CATCTGCCGG GAACTGAGAA GGAGGAAGTG AGAGAGAGCA
1001   TTGAGACCAA GTTCATTGCA TTCTGGTAG
```

FIG. 8

```
  1   MPHKDNLLES PVGKSVTATI AYHSGPALPT SPIAGVTTLQ DCTQQAVAVT
 51   DIRPSVSSFT LDGNGFQVVK HTSAVGSPPY DHSSWTDPVV RKEVYDPEII
101   ELAKSLTGAK KVMILLASSR NVPFKEPELA PPYPMPGKSS SGSKEREAIP
151   ANELPTTRAK GFQKGEEEGP VRKPHKDWGP SGAWNTLRNW SQELIDEAGD
201   IIKAGDEAAK LPGGRAKNYQ GRRWALYTTW RPLKTVKRDP MAYVDYWTAD
251   EEDGVSFWRN PPGVHGTFES DVLLTKANPK HKWYWISDQT PDEVLLMKIM
301   DTESEKDGSE IAGGVHHCSF HLPGTEKEEV RESIETKFIA FW
```

FIG. 9

| | | | | |
|---|---|---|---|---|
| 1 | | | ATGGTG | GCCATCACGG TGCCCATCTC |
| 27 | GGTGGACGCG | ATCCCTCTGG | TGAAATGCGC | ACATGCAGCG GCCGCGACGG |
| 77 | TGCCGAGCGT | CGACCTGTCG | GCGCCGGGCG | CGGCGGCGGC CGTCGCGGAC |
| 127 | GCGTGCCGCG | GCGTGGGCTT | CTTCAGGGCG | ACCATCCACG GCGTGCCGGC |
| 177 | CACCCTCACG | GACACTCTGG | AGGCCCGCGC | CGCGGCCTTC TTCACGCTGC |
| 227 | CGCACAAGGA | CAAGCTGGAG | GCGTCGGCGC | GGCCCTTGGG CTACGGCAGC |
| 277 | AAGAGCATCG | GCTGCAACGG | CGACGTGGGC | TGGCTCGAGT ACATCCTGCT |
| 327 | CTCCGTCGGG | TCCGGCTCGG | TCGCGGCGGC | CTCCCTGCCG CCGTCGCTCC |
| 377 | GGGCGGCGCT | CGAGGAGTAC | ACGGACGCG | TGCGGGAGGT GGGCGCGCGG |
| 427 | GTGCTGGAGC | TCATGGCGGA | TGGGCTCGGC | ATCGCGGTGG ACCACCGCGG |
| 477 | CGTGCTGCGG | CGGATGGTGG | CGTCGGACGA | AGCCGACGAG ATGGTGCGCG |
| 527 | TGAACCACTA | CCCGCCGTGC | CCCTGCCCCC | TAGCAGCAGG GCAGCGCGGC |
| 577 | GTGATGGGGT | TCGGGGAGCA | CACGGACCCG | CAGATCATCT CCGTGCTCCG |
| 627 | GTCCAACCGC | ACCGGGGGCC | TCCAGATCAT | GCTGCCGGAC GGCCGCTGGG |
| 677 | TCCCCGTGGC | CCCCGACCCC | GATTCCCTCT | TCGTCACTGT CGGGGACTCC |
| 727 | CTCCAGGTGC | TGACGAACGG | GCGGTTCCAG | AGCGTGAAGC ACCGGGTGGT |
| 777 | GGCGCCGGCG | GAGGGGCAGC | AGTCGCAGCT | GGTGCCGGTG AAGACGGAGT |
| 827 | CAGGGCTGGC | GCCCGTGAAG | ACGGAGCCGG | GCTGGCGCC GGTGAACGCG |
| 877 | GAGTTCGACG | ACGACGACGC | GGCCCTCGAA | TGGGCGCGCC AGGACTCCAT |
| 927 | CGCGTTGGAG | AAGGCGCGCC | GGGAGAAGGA | GAAGGAGCAC CAGTGTGCCG |
| 977 | CCCTACGCCG | CTTCGAGGAG | CGCCGACGCG | GCCGCGAGGA AGGCGGGGTC |
| 1027 | GTCGTCTTAT | GCGACAGCGA | CGACGATGAC | GACGTGCCGC CGCCTGTTCG |
| 1077 | CCAAGGCGAC | GCCGAGCAGG | GGTCCAGCAG | GGGCACCCGC GTCAAGGAGG |
| 1127 | AGAAGGCCGA | CGACGACGAT | GGCGGCGACG | ACTTCAGCCA CTTTCTTTTA |
| 1177 | CTTTAG | | | |

FIG. 10

| | | | | |
|---|---|---|---|---|
| 1 | MVAITVPISV | DAIPLVKCAH | AAAATVPSVD | LSAPGAAAAV ADACRGVGFF |
| 51 | RATIHGVPAT | LTDTLEARAA | AFFTLPHKDK | LEASARPLGY GSKSIGCNGD |
| 101 | VGWLEYILLS | VGSGSVAAAS | LPPSLRAALE | EYTDAVREVG ARVLELMADG |
| 151 | LGIAVDHRGV | LRRMVASDEA | DEMVRVNHYP | PCPCPLAAGQ RGVMGFGEHT |
| 201 | DPQIISVLRS | NRTGGLQIML | PDGRWVPVAP | DPDSLFVTVG DSLQVLTNGR |
| 251 | FQSVKHRVVA | PAEGQQSQLV | PVKTESGLAP | VKTEPGLAPV NAEFDDDDAA |
| 301 | LEWARQDSIA | LEKARREKEK | EHQCAALRRF | EERRRGREEG GVVVLCDSDD |
| 351 | DDDVPPPVRQ | GDAEQGSSRG | TRVKEEKADD | DDGGDDFSHF LLL |

FIG. 11

```
SEQUENCE LISTING

<160> NUMBER OF SEQ ID NOS: 13

<210> SEQ ID NO 1
<211> LENGTH: 1257
<212> TYPE: DNA
<213> ORGANISM: Artificial sequence
<220> FEATURE:
<223> OTHER INFORMATION: Nucleotide sequence of the promoter of the High
      Molecular Weight Glutenin-1-D1 gene from wheat with added PacI and
      StuI restriction sites at the 5prime and 3prime ends, respectively

<400> SEQUENCE: 1
ttaattaaaa atatgcaaca taatttcctt tttacttggc taattatatt tgataaatat      60
ttcacagata tacaataatc aaacacaata aatcatatgt gtttttagtt ttagttctca     120
tatccaaata tacaatagct aaccaaatct catcgggaag ttagccatgc cgaggtaggt     180
tgttgccgga atgtttttag ttttagttct catacaacca aatctcattc aaatatataa     240
aacattccgg caacaacttg tggcgtacat ctagttacaa gggaatatta gtgatggcgt     300
gagcaagcga taaggccaag gagagaagaa gtgcatcgtc tacggaggcc agggaaagac     360
aatggacatg cagagaggca ggggcgggga agaaacactt ggagatcata gaagaagata     420
agaggttaaa cataggagga ggatataatg gacaattaaa tctgcgttag ttgaactcat     480
ttgggaagta aacaaatttt ctattctgtg taaaccaaac tatttgacgc ggattttctc     540
tgaagatcct atattaattt tagacatggt ttggctagtt catttgtcgt gaaaaggtgt     600
```

-continued

```
ttccataagt ccaaaattct accaactttt ttgtatggca cgtcatagca tagatagatg      660
ttgtgagtca ctggatagat attgtgagtc atagcatgga ttcgtgttgc tggaaatcca      720
actacatgac aagcaacaaa acctgaaatg ggctttagga gttaacaatt tacttgttcc      780
atgcaggcta ccttccacta ctcgacatgc ttagaagctt tgagtggccg tagatttgca      840
aaagcaatgg ctaacagaca catattctgc caaaccccaa gaaggataat cacttttctt      900
agataaaaaa gaacgaccga atatacaaac atccacactt ctgcaaacaa tacatcagaa      960
ctaggattac gccgattacg tggctttagc agactgtcca aaaatctgtt ttgcaaagct     1020
ccaattgctc cttgcttatc cagcttcttt tgtgttggca aactgcgctt ttccaaccga     1080
ttttgttctt ctcgcgcttt cttcttaggc taaacaaacc tcaccgtgca cgcagccatg     1140
gtcctgaacc ttcacctcgt ccctataaaa gcctagccaa ccttcacaat cttatcatca     1200
cccacaacac cgagcaccac aaactagaga tcaattcact gatagtccac caggcct      1257
```

<210> SEQ ID NO 2
<211> LENGTH: 1146
<212> TYPE: DNA
<213> ORGANISM: Artificial sequence
<220> FEATURE:
<223> OTHER INFORMATION: Nucleotide sequence of the promoter of the
      coding region of the gibberellin 20-oxidase-1 gene from
      Arabidopsis thaliana with added XhoI and SacI sites at the 5prime
      and 3prime ends, respectively

<400> SEQUENCE: 2

```
ctcgagatgg ccgtaagttt cgtaacaaca tctcctgagg aagaagacaa accgaagcta       60
ggccttggaa atattcaaac tccgttaatc ttcaacccct caatgcttaa ccttcaagcc      120
aatatcccaa accaattcat ctggcctgac gacgaaaaac cttccatcaa cgttctcgag      180
cttgatgttc ctctcatcga ccttcaaaac cttctctctg atccatcctc cactttagat      240
gcttcgagac tgatctctga ggcctgtaag aagcacggtt tcttcctcgt ggtcaatcac      300
ggcatcagcg aggagcttat atcagacgct catgaataca cgagccgctt cttttgatatg      360 cctctctccg aaaaacagag ggttcttaga aaatccggtg agagtgttgg ctacgcaagc      420
agtttcaccg gacgcttctc caccaagctt ccatggaagg agacccttc tttccggttt      480 tgcgacgaca tgagccgctc aaaatccgtt caagattact tctgcgatgc gttgggacat      540
gggtttcagc catttgggaa ggtgtatcaa gagtattgtg aagcaatgag ttctctatca      600
ttgaagatca tggagcttct cgggctaagt ttaggcgtaa aacgggacta ctttagagag      660
tttttcgaag aaaacgattc aataatgaga ctgaattact accctccatg tataaaacca      720
gatctcacac taggaacagg acctcattgt gatccaacat ctcttaccat ccttcaccaa      780
gaccatgtta atggccttca agtctttgtg gaaaatcaat ggcgctccat tcgtcccaac      840
cccaaggcct ttgtggtcaa tatcggcgat actttcatgg ctctatcgaa cgatagatac      900
aagagctgct tgcaccgggc ggtggtgaac agcaagagcg agaggaagtc acttgcattc      960
ttcttgtgtc cgaaaaaaga cagagtagtg acgccaccga gagagctttt ggacagcatc     1020
acatcaagaa gatacccctga cttcacatgg tctatgttcc ttgagttcac tcagaaacat     1080
tatagagcag acatgaacac tctccaagcc ttttcagatt ggctcaccaa acccatctaa     1140
gagctc                                                               1146
```

<210> SEQ ID NO 3
<211> LENGTH: 377
<212> TYPE: PRT
<213> ORGANISM: Arabidopsis thaliana

<400> SEQUENCE: 3

```
Met Ala Val Ser Phe Val Thr Thr Ser Pro Glu Glu Asp Lys Pro
1               5                   10                  15

Lys Leu Gly Leu Gly Asn Ile Gln Thr Pro Leu Ile Phe Asn Pro Ser
            20                  25                  30

Met Leu Asn Leu Gln Ala Asn Ile Pro Asn Gln Phe Ile Trp Pro Asp
            35                  40                  45

Asp Glu Lys Pro Ser Ile Asn Val Leu Glu Leu Asp Val Pro Leu Ile
        50                  55                  60

Asp Leu Gln Asn Leu Leu Ser Asp Pro Ser Ser Thr Leu Asp Ala Ser
65                  70                  75                  80

Arg Leu Ile Ser Glu Ala Cys Lys Lys His Gly Phe Phe Leu Val Val
                85                  90                  95

Asn His Gly Ile Ser Glu Glu Leu Ile Ser Asp Ala His Glu Tyr Thr
            100                 105                 110

Ser Arg Phe Phe Asp Met Pro Leu Ser Glu Lys Gln Arg Val Leu Arg
        115                 120                 125

Lys Ser Gly Glu Ser Val Gly Tyr Ala Ser Ser Phe Thr Gly Arg Phe
    130                 135                 140

Ser Thr Lys Leu Pro Trp Lys Glu Thr Leu Ser Phe Arg Phe Cys Asp
145                 150                 155                 160

Asp Met Ser Arg Ser Lys Ser Val Gln Asp Tyr Phe Cys Asp Ala Leu
                165                 170                 175

Gly His Gly Phe Gln Pro Phe Gly Lys Val Tyr Gln Glu Tyr Cys Glu
            180                 185                 190

Ala Met Ser Ser Leu Ser Leu Lys Ile Met Glu Leu Leu Gly Leu Ser
        195                 200                 205

Leu Gly Val Lys Arg Asp Tyr Phe Arg Glu Phe Phe Glu Glu Asn Asp
    210                 215                 220

Ser Ile Met Arg Leu Asn Tyr Tyr Pro Pro Cys Ile Lys Pro Asp Leu
225                 230                 235                 240

Thr Leu Gly Thr Gly Pro His Cys Asp Pro Thr Ser Leu Thr Ile Leu
                245                 250                 255

His Gln Asp His Val Asn Gly Leu Gln Val Phe Val Glu Asn Gln Trp
            260                 265                 270

Arg Ser Ile Arg Pro Asn Pro Lys Ala Phe Val Val Asn Ile Gly Asp
        275                 280                 285

Thr Phe Met Ala Leu Ser Asn Asp Arg Tyr Lys Ser Cys Leu His Arg
    290                 295                 300

Ala Val Val Asn Ser Lys Ser Glu Arg Lys Ser Leu Ala Phe Phe Leu
305                 310                 315                 320

Cys Pro Lys Lys Asp Arg Val Val Thr Pro Arg Glu Leu Leu Asp
                325                 330                 335

Ser Ile Thr Ser Arg Arg Tyr Pro Asp Phe Thr Trp Ser Met Phe Leu
            340                 345                 350

Glu Phe Thr Gln Lys His Tyr Arg Ala Asp Met Asn Thr Leu Gln Ala
        355                 360                 365

Phe Ser Asp Trp Leu Thr Lys Pro Ile
    370                 375
```

<210> SEQ ID NO 4
<211> LENGTH: 1077
<212> TYPE: DNA
<213> ORGANISM: Arabidopsis thaliana -continued

<400> SEQUENCE: 4

```
atgcctgcta tgttaacaga tgtgtttaga ggccatccca ttcacctccc acactctcac      60
atacctgact tcacatctct ccgggagctc ccggattctt acaagtggac ccctaaagac     120
gatctcctct tctccgctgc tccttctcct ccggccaccg gtgaaaacat ccctctcatc     180
gacctcgacc acccggacgc gactaaccaa atcggtcatg catgtagaac ttggggtgcc     240
ttccaaatct caaccacgg cgtgcctttg ggacttctcc aagacattga gtttctcacc     300
ggtagtctct tcgggctacc tgtccaacgc aagcttaagt ctgctcggtc ggagacaggt     360
gtgtccggct acgcgtcgc tcgtatcgca tctttcttca ataagcaaat gtggtccgaa     420
ggtttcacca tcactggctc gcctctcaac gatttccgta aactttggcc ccaacatcac     480
ctcaactact gcgatatcgt tgaagagtac gaggaacata tgaaaaagtt ggcatcgaaa     540
ttgatgtggt tagcactaaa ttcacttggg gtcagcgaag aagacattga atgggccagt     600
ctcagttcag atttaaactg ggcccaagct gctctccagc taaatcacta cccggtttgt     660
cctgaaccgg accgagccat gggtctagca gctcataccg actccaccct cctaaccatt     720
ctgtaccaga caataccgc cggtctacaa gtatttcgcg atgatcttgg ttgggtcacc     780
gtgccaccgt ttcctggctc gctcgtggtt aacgttggtg acctcttcca catcctatcc     840
aatggattgt ttaaaagcgt gttgcaccgc gctcgggtta accaaaccag agcccggtta     900
tctgtagcat tccttgggg tccgcaatct gatatcaaga tatcacctgt accgaagctg     960
gttagtcccg ttgaatcgcc tctataccaa tcggtgacat ggaaagagta tcttcgaaca    1020
aaagcaactc acttcaacaa agctctttca atgattagaa atcacagaga agaatga      1077
```

<210> SEQ ID NO 5
<211> LENGTH: 1029
<212> TYPE: DNA
<213> ORGANISM: Gibberella fujikuroi

<400> SEQUENCE: 5

```
atgcctcata aagataatct tcttgaatcg ccagtgggca agagtgtcac tgctactata      60
gcctaccata gcgaccggc tcttccaacc tccccgatcg ctggtgtcac tacgctccaa     120
gactgcactc agcaggccgt agcagtgact gatatccgcc cttcagtctc gtcctttacc     180
ctagatggta acggcttcca ggttgtcaaa catacatcgg cggtaggctc tccgccgtat     240
gatcactcgt cgtggacaga tccagtcgtt cgcaaggaag tgtatgaccc cgaaatcatt     300
gaactggcaa agtctctcac tggagccaag aaggtcatga ttctacttgc ttcgtctcgg     360
aatgttccct tcaaggagcc agagctcgcc cctccttatc ccatgcctgg caaatcaagc     420
agcggcagca aggaaaggga agccatccca gctaatgagc tccctactac aagggcaaaa     480
ggtttccaaa aaggcgaaga ggaaggccca gtacgaaagc tcataaggga ctggggtcca     540
tccggtgcgt ggaacactct ccggaactgg agccaagagc tcattgatga ggctggcgat     600
atcatcaagg ctggcgatga ggctgcaaag ctgccagggg gcagagcaaa gaactaccaa     660
ggcagacgat gggccctgta tactacctgg cgtccactga aaactgtcaa gcgggatccc     720
atggcctatg tagactactg gacagctgat gaggaagatg gcgtgagctt ctggcgtaac     780
ccgccagggg tgcatggac atttgagtcg gatgtactac ttaccaaggc taatccaaag     840
cataagtggt actggatcag tgaccagact ccggatgagg ttctcctcat gaagatcatg     900
gacaccgaga gtgagaagga cgggagtgaa atagcgggag gggttcacca ctgttcattt     960
```

```
catctgccgg gaactgagaa ggaggaagtg agagagagca ttgagaccaa gttcattgca    1020
ttctggtag                                                            1029
```

<210> SEQ ID NO 6
<211> LENGTH: 358
<212> TYPE: PRT
<213> ORGANISM: Arabidopsis thaliana

<400> SEQUENCE: 6

```
Met Pro Ala Met Leu Thr Asp Val Phe Arg Gly His Pro Ile His Leu
1               5                   10                  15

Pro His Ser His Ile Pro Asp Phe Thr Ser Leu Arg Glu Leu Pro Asp
            20                  25                  30

Ser Tyr Lys Trp Thr Pro Lys Asp Asp Leu Leu Phe Ser Ala Ala Pro
        35                  40                  45

Ser Pro Pro Ala Thr Gly Glu Asn Ile Pro Leu Ile Asp Leu Asp His
    50                  55                  60

Pro Asp Ala Thr Asn Gln Ile Gly His Ala Cys Arg Thr Trp Gly Ala
65                  70                  75                  80

Phe Gln Ile Ser Asn His Gly Val Pro Leu Gly Leu Leu Gln Asp Ile
                85                  90                  95

Glu Phe Leu Thr Gly Ser Leu Phe Gly Leu Pro Val Gln Arg Lys Leu
            100                 105                 110

Lys Ser Ala Arg Ser Glu Thr Gly Val Ser Gly Tyr Gly Val Ala Arg
        115                 120                 125

Ile Ala Ser Phe Phe Asn Lys Gln Met Trp Ser Glu Gly Phe Thr Ile
    130                 135                 140

Thr Gly Ser Pro Leu Asn Asp Phe Arg Lys Leu Trp Pro Gln His His
145                 150                 155                 160

Leu Asn Tyr Cys Asp Ile Val Glu Glu Tyr Glu Glu His Met Lys Lys
                165                 170                 175

Leu Ala Ser Lys Leu Met Trp Leu Ala Leu Asn Ser Leu Gly Val Ser
            180                 185                 190

Glu Glu Asp Ile Glu Trp Ala Ser Leu Ser Ser Asp Leu Asn Trp Ala
        195                 200                 205

Gln Ala Ala Leu Gln Leu Asn His Tyr Pro Val Cys Pro Glu Pro Asp
    210                 215                 220

Arg Ala Met Gly Leu Ala Ala His Thr Asp Ser Thr Leu Leu Thr Ile
225                 230                 235                 240

Leu Tyr Gln Asn Asn Thr Ala Gly Leu Gln Val Phe Arg Asp Asp Leu
                245                 250                 255

Gly Trp Val Thr Val Pro Pro Phe Pro Gly Ser Leu Val Val Asn Val
            260                 265                 270

Gly Asp Leu Phe His Ile Leu Ser Asn Gly Leu Phe Lys Ser Val Leu
        275                 280                 285

His Arg Ala Arg Val Asn Gln Thr Arg Ala Arg Leu Ser Val Ala Phe
    290                 295                 300

Leu Trp Gly Pro Gln Ser Asp Ile Lys Ile Ser Pro Val Pro Lys Leu
305                 310                 315                 320

Val Ser Pro Val Glu Ser Pro Leu Tyr Gln Ser Val Thr Trp Lys Glu
                325                 330                 335

Tyr Leu Arg Thr Lys Ala Thr His Phe Asn Lys Ala Leu Ser Met Ile
            340                 345                 350

Arg Asn His Arg Glu Glu
        355
```

```
<210> SEQ ID NO 7
<211> LENGTH: 342
<212> TYPE: PRT
<213> ORGANISM: Gibberella fujikuroi

<400> SEQUENCE: 7

Met Pro His Lys Asp Asn Leu Leu Glu Ser Pro Val Gly Lys Ser Val
1               5                   10                  15

Thr Ala Thr Ile Ala Tyr His Ser Gly Pro Ala Leu Pro Thr Ser Pro
            20                  25                  30

Ile Ala Gly Val Thr Thr Leu Gln Asp Cys Thr Gln Gln Ala Val Ala
        35                  40                  45

Val Thr Asp Ile Arg Pro Ser Val Ser Ser Phe Thr Leu Asp Gly Asn
    50                  55                  60

Gly Phe Gln Val Val Lys His Thr Ser Ala Val Gly Ser Pro Pro Tyr
65                  70                  75                  80

Asp His Ser Ser Trp Thr Asp Pro Val Val Arg Lys Glu Val Tyr Asp
                85                  90                  95

Pro Glu Ile Ile Glu Leu Ala Lys Ser Leu Thr Gly Ala Lys Lys Val
            100                 105                 110

Met Ile Leu Leu Ala Ser Ser Arg Asn Val Pro Phe Lys Glu Pro Glu
        115                 120                 125

Leu Ala Pro Pro Tyr Pro Met Pro Gly Lys Ser Ser Ser Gly Ser Lys
    130                 135                 140

Glu Arg Glu Ala Ile Pro Ala Asn Glu Leu Pro Thr Thr Arg Ala Lys
145                 150                 155                 160

Gly Phe Gln Lys Gly Glu Glu Glu Gly Pro Val Arg Lys Pro His Lys
                165                 170                 175

Asp Trp Gly Pro Ser Gly Ala Trp Asn Thr Leu Arg Asn Trp Ser Gln
            180                 185                 190

Glu Leu Ile Asp Glu Ala Gly Asp Ile Ile Lys Ala Gly Asp Glu Ala
        195                 200                 205

Ala Lys Leu Pro Gly Gly Arg Ala Lys Asn Tyr Gln Gly Arg Arg Trp
    210                 215                 220

Ala Leu Tyr Thr Thr Trp Arg Pro Leu Lys Thr Val Lys Arg Asp Pro
225                 230                 235                 240

Met Ala Tyr Val Asp Tyr Trp Thr Ala Asp Glu Glu Asp Gly Val Ser
                245                 250                 255

Phe Trp Arg Asn Pro Pro Gly Val His Gly Thr Phe Glu Ser Asp Val
            260                 265                 270

Leu Leu Thr Lys Ala Asn Pro Lys His Lys Trp Tyr Trp Ile Ser Asp
        275                 280                 285

Gln Thr Pro Asp Glu Val Leu Leu Met Lys Ile Met Asp Thr Glu Ser
    290                 295                 300

Glu Lys Asp Gly Ser Glu Ile Ala Gly Gly Val His His Cys Ser Phe
305                 310                 315                 320

His Leu Pro Gly Thr Glu Lys Glu Glu Val Arg Glu Ser Ile Glu Thr
                325                 330                 335

Lys Phe Ile Ala Phe Trp
            340

<210> SEQ ID NO 8
<211> LENGTH: 1182
<212> TYPE: DNA
<213> ORGANISM: Triticum aestivum
```

<400> SEQUENCE: 8

```
atggtggcca tcacggtgcc catctcggtg gacgcgatcc ctctggtgaa atgcgcacat    60
gcagcggccg cgacggtgcc gagcgtcgac ctgtcggcgc cgggcgcggc ggcggccgtc   120
gcggacgcgt gccgcggcgt gggcttcttc agggcgacca tccacggcgt gccggccacc   180
ctcacggaca ctctggaggc ccgcgccgcg gccttcttca cgctgccgca caaggacaag   240
ctggaggcgt cggcgcggcc cttgggctac ggcagcaaga gcatcggctg caacggcgac   300
gtgggctggc tcgagtacat cctgctctcc gtcgggtccg gctcggtcgc ggcggcctcc   360
ctgccgccgt cgctccgggc ggcgctcgag gagtacacgg acgcggtgcg ggaggtgggc   420
gcgcgggtgc tggagctcat ggcggatggg ctcggcatcg cggtggacca ccgcggcgtg   480
ctgcggcgga tggtggcgtc ggacgaagcc gacgagatgg tgcgcgtgaa ccactacccg   540
ccgtgcccct gcccctagc agcagggcag cgcggcgtga tggggttcgg ggagcacacg   600
gacccgcaga tcatctccgt gctccggtcc aaccgcaccg gggcctcca gatcatgctg   660
ccggacggcc gctgggtccc cgtggccccc gaccccgatt ccctcttcgt cactgtcggg   720
gactccctcc aggtgctgac gaacgggcgg ttccagagcg tgaagcaccg ggtggtggcg   780
ccggcggagg ggcagcagtc gcagctggtg ccggtgaaga cggagtcagg gctggcgccc   840
gtgaagacgg agccggggct ggcgccggtg aacgcggagt cgacgacga cgacgcggcc   900
ctcgaatggg cgcgccagga ctccatcgcg ttggagaagg cgcgccggga aaggagaag   960
gagcaccagt gtgccgccct acgccgcttc gaggagcgcc gacgcggccg cgaggaaggc  1020
ggggtcgtcg tcttatgcga cagcgacgac gatgacgacg tgccgccgcc tgttcgccaa  1080
ggcgacgccg agcaggggtc cagcaggggc acccgcgtca aggaggagaa ggccgacgac  1140
gacgatggcg gcgacgactt cagccacttt cttttacttt ag                     1182
```

<210> SEQ ID NO 9
<211> LENGTH: 393
<212> TYPE: PRT
<213> ORGANISM: Triticum aestivum

<400> SEQUENCE: 9

```
Met Val Ala Ile Thr Val Pro Ile Ser Val Asp Ala Ile Pro Leu Val
1               5                  10                  15

Lys Cys Ala His Ala Ala Ala Ala Thr Val Pro Ser Val Asp Leu Ser
            20                  25                  30

Ala Pro Gly Ala Ala Ala Val Ala Asp Ala Cys Arg Gly Val Gly
        35                  40                  45

Phe Phe Arg Ala Thr Ile His Gly Val Pro Ala Thr Leu Thr Asp Thr
    50                  55                  60

Leu Glu Ala Arg Ala Ala Ala Phe Phe Thr Leu Pro His Lys Asp Lys
65                  70                  75                  80

Leu Glu Ala Ser Ala Arg Pro Leu Gly Tyr Gly Ser Lys Ser Ile Gly
                85                  90                  95

Cys Asn Gly Asp Val Gly Trp Leu Glu Tyr Ile Leu Leu Ser Val Gly
            100                 105                 110

Ser Gly Ser Val Ala Ala Ala Ser Leu Pro Pro Ser Leu Arg Ala Ala
        115                 120                 125

Leu Glu Glu Tyr Thr Asp Ala Val Arg Glu Val Gly Ala Arg Val Leu
    130                 135                 140

Glu Leu Met Ala Asp Gly Leu Gly Ile Ala Val Asp His Arg Gly Val
145                 150                 155                 160
```

```
Leu Arg Arg Met Val Ala Ser Asp Glu Ala Asp Glu Met Val Arg Val
                165                 170                 175
Asn His Tyr Pro Pro Cys Pro Cys Pro Leu Ala Ala Gly Gln Arg Gly
            180                 185                 190
Val Met Gly Phe Gly Glu His Thr Asp Pro Gln Ile Ile Ser Val Leu
        195                 200                 205
Arg Ser Asn Arg Thr Gly Gly Leu Gln Ile Met Leu Pro Asp Gly Arg
    210                 215                 220
Trp Val Pro Val Ala Pro Asp Pro Asp Ser Leu Phe Val Thr Val Gly
225                 230                 235                 240
Asp Ser Leu Gln Val Leu Thr Asn Gly Arg Phe Gln Ser Val Lys His
                245                 250                 255
Arg Val Val Ala Pro Ala Glu Gly Gln Gln Ser Gln Leu Val Pro Val
            260                 265                 270
Lys Thr Glu Ser Gly Leu Ala Pro Val Lys Thr Glu Pro Gly Leu Ala
        275                 280                 285
Pro Val Asn Ala Glu Phe Asp Asp Asp Ala Ala Leu Glu Trp Ala
    290                 295                 300
Arg Gln Asp Ser Ile Ala Leu Glu Lys Ala Arg Arg Glu Lys Glu Lys
305                 310                 315                 320
Glu His Gln Cys Ala Ala Leu Arg Arg Phe Glu Glu Arg Arg Gly
                325                 330                 335
Arg Glu Glu Gly Gly Val Val Leu Cys Asp Ser Asp Asp Asp Asp
            340                 345                 350
Asp Val Pro Pro Pro Val Arg Gln Gly Asp Ala Glu Gln Gly Ser Ser
    355                 360                 365
Arg Gly Thr Arg Val Lys Glu Glu Lys Ala Asp Asp Asp Gly Gly
        370                 375                 380
Asp Asp Phe Ser His Phe Leu Leu Leu
385                 390

<210> SEQ ID NO 10
<211> LENGTH: 31
<212> TYPE: DNA
<213> ORGANISM: Artificial sequence
<220> FEATURE:
<223> OTHER INFORMATION: Primer HMW-L

<400> SEQUENCE: 10
aaattaatta aaaatatgca acataatttc c                              31

<210> SEQ ID NO 11
<211> LENGTH: 29
<212> TYPE: DNA
<213> ORGANISM: Artificial sequence
<220> FEATURE:
<223> OTHER INFORMATION: Primer HMW-R

<400> SEQUENCE: 11
aaaaggcctg gtggactatc agtaattga                                 29

<210> SEQ ID NO 12
<211> LENGTH: 29
<212> TYPE: DNA
<213> ORGANISM: Artificial sequence
<220> FEATURE:
<223> OTHER INFORMATION: Primer 20ox1-L

<400> SEQUENCE: 12
aaactcgaga tggccgtaag tttcgtaac                                 29
```

```
<210> SEQ ID NO 13
<211> LENGTH: 29
<212> TYPE: DNA
<213> ORGANISM: Artificial sequence
<220> FEATURE:
<223> OTHER INFORMATION: Primer 20ox1-R

<400> SEQUENCE: 13
aaagagctct tagatgggtt tggtgagcc                                          29
```

METHOD FOR INCREASING SEED SIZE BY INCREASING GIBBERELLIN CONTENT IN THE SEEDS

The present invention relates to a method for increasing the size of plant seed which may be characterised as an increase in seed weight or seed volume.

Techniques of plant breeding have developed from traditional methods to the use of recombinant DNA technology to introduce desirable genetic characteristics into plants, particularly agricultural crop plant species, of interest.

Previous studies in this area have discovered that plant growth can be regulated by the expression of enzymes important in the biosynthesis of gibberellins (GAs). The gibberellins (GAs) are a large group of diterpenoid carboxylic acids that are present in all higher plants and some fungi. Certain members of the group function as plant hormones and are involved in many developmental processes, including seed germination, stem extension, leaf expansion, flower initiation and development, and growth of the seeds and fruit. The biologically active GAs are usually $C_{19}$ compounds containing a 19-10 lactone, a C-7 carboxylic acid and a 3β-hydroxyl group. The later stages of their biosynthesis involve the oxidative removal of C-20 and hydroxylation at C-3. Hydroxylation at the 2β position results in the production of biologically inactive products. This reaction is the most important route for GA metabolism in plants and ensures that the active hormones do not accumulate in plant tissues. The GA biosynthetic enzymes 7-oxidase, 20-oxidase, 3β-hydroxylase and 2β-hydroxylase are all 2-oxoglutarate-dependent dioxygenases. These are a large group of enzymes for which 2-oxoglutarate is a co-substrate that is decarboxylated to succinate as part of the reaction (see review by Hedden, P. and Kamiya, Y., in *Annu. Rev. Plant Physiol. Plant Mol. Biol.* 48 431-460 (1997)).

Chemical regulators of plant growth have been used in horticulture and agriculture for many years. Many of these compounds function by changing the GA concentration in plant tissues. For example, growth retardants inhibit the activity of enzymes involved in GA biosynthesis and thereby reduce the GA content. Such chemicals are used commonly, for example, to prevent lodging in cereals and to control the growth of ornamental and horticultural plants. Conversely, GAs may be applied to plants, such as in the application of $GA_3$ to seedless grapes to improve the size and shape of the berry, and to barley grain to improve malt production. Mixtures of $GA_4$ and $GA_7$ are applied to apples to improve fruit quality and to certain conifers to stimulate cone production. There are several problems associated with the use of growth regulators. Some of the growth retardants are highly persistent in the soil making it difficult to grow other crops following a treated crop. Others require repeated applications to maintain the required effect. It is difficult to restrict application to the target plant organs without it spreading to other organs or plants and having undesirable effects. Precise targeting of the growth-regulator application can be very labour intensive. A non-chemical option for controlling plant morphology is, thus, highly desirable.

Gibberellin biosynthesis has been modified in transgenic plants. See for example WO 94/28141 which reports the cloning and expression of a gibberellin (GA) 20-oxidase gene which catalyses the penultimate step in GA biosynthesis, or WO 99/66029 which reports the cloning and expression of nucleic acid sequences encoding a gibberellin 2β-hydroxylase enzyme (GA 2-oxidase) which is a gibberellin inactivation enzyme. It catalyses the 2β-oxidation (2-oxidation) of a gibberellin molecule to introduce a hydroxyl group at C-2 and further catalyses the oxidation of the hydroxyl group introduced at C-2 to yield the ketone derivative.

A system of nomenclature for the GA-biosynthesis genes has now been introduced (Coles et al *The Plant Journal* 17(5) 547-556 (1999). References to "gibberellin" include all bioactive gibberellin molecules, unless the context specifies otherwise.

It has long been an aim in agriculture to be able to increase the size of seeds produced by plant species of interest. For many plants, the seeds are the main product to be harvested and an increase in size would be beneficial in improving overall crop yields. For all agricultural plant species, an increase in seed size may assist in the success of planting out a crop by providing the developing plant with a larger resource for germination of the seed.

It has now been surprisingly found that by manipulation of the expression of gibberellin enzymes that an increase in the size of seeds can be achieved.

According to a first aspect of the invention, there is provided a method of increasing the weight of plant seed, the method comprising preparing a genetically modified plant in which gibberellin content has been manipulated in the seed of the plant.

The plant seeds produced according to a method of the invention have an increased size in comparison to plant seeds from control plants. An increase in the size of seed of a plant can be characterised by an increase in volume of the seed as well as by its weight.

Plant seeds are the ripened plant ovule containing an embryo of a gymnosperm or an angiosperm plant.

Preferred species of plants include but are not limited to monocotyledonous plants including seed and the progeny or propagules thereof, for example *Lolium*, *Zea*, *Triticum*, *Sorghum*, *Triticale*, *Saccharum*, *Bromus*, *Oryzae*, *Avena*, *Hordeum*, *Secale* and *Setaria*. Especially useful transgenic plants are maize, wheat, barley plants and seed thereof. Suitably the monocotyledonous is selected from the group consisting of wheat, maize, rye, rice, oat, barley, sorghum and millet.

Dicotyledenous plants are also within the scope of the present invention and preferred transgenic plants include but are not limited to the species *Fabaceae*, *Solanum*, *Brassicaceae*, especially potatoes, beans, cabbages, forest trees, roses, clematis, oilseed rape, sunflower, chrysanthemum, poinsettia and antirrhinum (snapdragon). Alternatively, the transgenic plant may be a dicotyledonous plant. Suitably, the dicotyledonous is selected from the group consisting of soybean, canola, and sunflower.

Genetically modified plants according to a method of the invention may be prepared by any convenient procedure, examples of which are described below. The plants are modified to express a nucleic acid sequence encoding an enzyme of gibberellin biosynthesis, or an enzyme which renders gibberellins resistant to inactivation, or to express nucleic acid molecules to inhibit the expression of enzymes of gibberellin inactivation, or to otherwise manipulate the content of gibberellin in the seed, such as for example by mutagenesis, conveniently by chemical mutagenesis. Expression of a nucleic acid sequence includes overexpression above basal or endogenous levels, which can be defined with respect to levels of expression in an unaltered or control plant of the same species. Expression of such nucleic acid sequences therefore includes expression of an exogenous gene introduced into the plant, as well as introduction of promoter sequences to drive expression of the endogenous gene, such as, for example, homologous recombination.

The nucleic acid sequence may be as shown in any one of FIG. 4, 6, 8, or 10, or its complementary strand or a homologous sequence thereto. Alternatively, the nucleic acid may be a nucleic acid sequence that encodes an amino acid sequence or a protein sequence as shown in any one of FIG. 5, 7, 9, or 11, or its complementary strand or a homologous sequence thereto.

In the context of the present invention, the degree of identity between amino acid sequences may be at least 40%, suitably 50% or higher, e.g. 55%, 60%, 65%, 70%, 75%, 80%, 85%, 90% or 95%. At the nucleotide level, the degree of identity may be at least 50%, suitably 60% or higher, e.g. 65%, 70%, 75%, 80%, 85%, 90% or 95%. A homologous sequence according to the present invention may therefore have a sequence identity as described above. Sequence homology may be determined using any conveniently available protocol, for example using Clustal X™ from the University of Strasbourg and the tables of identities produced using Genedoc™ (Karl B. Nicholas).

Also included within the scope of the present invention are nucleic acid sequences which hybridises to a sequence in accordance with the first aspect of the invention under stringent conditions, or a nucleic acid sequence which is homologous to or would hybridise under stringent conditions to such a sequence but for the degeneracy of the genetic code, or an oligonucleotide sequence specific for any such sequence.

Stringent conditions of hybridisation may be characterised by low salt concentrations or high temperature conditions. For example, highly stringent conditions can be defined as being hybridisation to DNA bound to a solid support in 0.5 M NaHPO$_4$, 7% sodium dodecyl sulfate (SDS), 1 mM EDTA at 65° C., and washing in 0.1×SSC/0.1% SDS at 68° C. (Ausubel et al eds. "*Current Protocols in Molecular Biology*" 1, page 2.10.3, published by Green Publishing Associates, Inc. and John Wiley & Sons, Inc., New York, (1989)). In some circumstances less stringent conditions may be required. As used in the present application, moderately stringent conditions can be defined as comprising washing in 0.2×SSC/0.1% SDS at 42° C. (Ausubel et al (1989) supra). Hybridisation can also be made more stringent by the addition of increasing amounts of formamide to destabilise the hybrid nucleic acid duplex. Thus particular hybridisation conditions can readily be manipulated, and will generally be selected according to the desired results. In general, convenient hybridisation temperatures in the presence of 50% formamide are 42° C. for a probe which is 95 to 100% homologous to the target DNA, 37° C. for 90 to 95% homology, and 32° C. for 70 to 90% homology.

Expression of a nucleic acid sequence encoding an enzyme of gibberellin metabolism (i.e. an enzyme of gibberellin biosynthesis or catabolism) may comprise expression of (i) the enzyme gibberellin 20-oxidase (GA20ox), that catalyses the penultimate steps in GA biosynthesis, as in the example included (FIGS. 4 & 5); or (ii) the enzyme gibberellin 3β-hydroxylase (GA 3-oxidase, GA3ox, eg. AtGA3ox1, FIGS. 6 & 7) that catalyses the last step in GA biosynthesis, eg. AtGA3ox1, Genbank No. L37126, Chiang H H et al., Plant Cell 7:195-201; 1995). Expression includes overexpression above basal or endogenous levels.

Expression of a nucleic acid sequence encoding an enzyme which renders gibberellins resistant to inactivation may comprise production of the enzyme gibberellin 1,2-desaturase (eg. FIGS. 8 & 9) which renders GAs resistant to inactivation (GAdes; Genbank No. AJ417493, Tudzynski B, et al., J. Biol. Chem. 278:28635-28643; 2003). Expression includes overexpression above basal or endogenous levels, for example overexpression of the nucleic acid may comprise overproduction of the enzyme with respect to basal or endogenous levels of expression.

Expression of nucleic acid molecules to inhibit the expression of enzymes of gibberellin inactivation (i.e. by reduction or abolition of gene expression) may comprise reduction in activity or concentration of the endogenous gibberellin inactivation enzyme gibberellin 2β-hydroxylase (GA 2-oxidase; GA2ox, eg. FIGS. 10 & 11: TaGA2ox2).

Mutagenesis of the plant may be conveniently achieved by any technique of chemical or radionucleide-induced mutagenesis, or for example by TILLING (McCallum C M, et al., Plant Physiol. 123:439-442; 2000).

Other nucleic acid sequences in accordance with this aspect of the present invention may also comprise a nucleic acid sequence as previously defined in which the coding sequence is operatively linked to a promoter. The promoter may be constitutive and/or specific for expression in a particular plant cell or tissue, preferably in seeds.

Preferably, the nucleic acid sequence comprises a promoter which drives expression of a nucleic acid sequence described above. Such promoter sequences include promoters which occur naturally 5' to the coding sequence of the sequences shown in FIG. 4, 6, 8, or 10. Promoters may also be selected to constitutively express the nucleic acid coding for the preferred gene sequences defined herein. Expression of the nucleic acid includes overexpression above basal or endogenous levels. Promoters that are induced by internal or external factors, such as chemicals, plant hormones, light or stress could also be used. Examples are the pathogenesis related genes inducible by salicylic acid, copper-controllable gene expression (Mett et al *Proc. Nat'l. Acad. Sci. USA* 90 4567-4571 (1993)) and tetracycline-regulated gene expression (Gatz et al *Plant Journal* 2 397-404 (1992)). Examples of gibberellin-inducible genes are γ-TIP (Phillips, A. L., & Huttly, A. K., *Plant Mol. Biol.* 24 603-615 (1994)) and GAST (Jacobsen, S. E., & Olszewski, N. E., *Planta* 198 78-86 (1996).

Suitable promoters for driving transgene expression in developing seeds include:
(i) High Molecular Weight Glutenin-1-D1 promoter from Wheat (FIG. 3; Lamacchia et al., 2001);
(ii) End-1 promoter from barley (Clarke B C, et al., Aust. J. Agric. Res. 52:1181-1193; 2001).
(iii) MAC1 promoter from maize (Sheridan et al., Genetics 142:1009-1020, 1996);
(iv) Cat3 promoter from maize (GenBank No. L05934, Abler et al., Plant Mol. Biol. 22:10131-1038, 1993);
(v) Atimyc1 from *Arabidopsis* (Urao et al., Plant J. Mol. Biol. 32:571-57, 1996; Conceicao et al., Plant 5:493-505, 1994);
(vi) napA from Brassica napus (GenBank No. J02798);
(vii) Napin gene family from Brassica napus (Sjodahl et al., Planta 197:264-271, 1995);
(viii) 2S storage protein promoter from Brassica napus (Dasgupta et al., Gene 133:301-302, 1993);
(ix) 2S seed storage protein gene family promoter from *Arabidopsis;*
(x) Oleosin 20 kD from Brassica napus (GenBank No. M63985);
(xi) Oleosin A promoter (GenBank No. U09118) or Oleosin B promoter (GenBank No. U09119) from soybean;
(xii) Oleosin promoter from *Arabidopsis* (GenBank No. Z17657);
(xiii) Oleosin 18 kD promoter from maize (GenBank No. J05212, Lee, Plant Mol. Biol. 26:1981-1987, 1994);
(xiv) Low molecular weight sulphur rich protein promoter from soybean (Choi et al., Mol. Gen. Genet. 246:266-268, 1995);

(xv) Promoters derived from zein-encoding genes (including the 15 kD, 16 kD, 19 kD, 22 kD, 27 kD, and gamma-zein genes, Pedersen et al., Cell 29:1015-1026, 1982).

The rice actin-1 intron may also be used to increase transgene mRNA accumulation, but this is not necessary for the invention.

The nucleic acid sequences of the present invention may also code for RNA which is antisense to the RNA normally found in a plant cell or may code for RNA which is capable of cleavage of RNA normally found in a plant cell. In such an approach, the whole cDNA or smaller fragments (>200 bp) may be amplified by PCR and inserted into an appropriate expression vector in reverse orientation to the primer. Accordingly, the present invention also provides a nucleic acid sequence encoding a ribozyme capable of specific cleavage of RNA encoded by a gene for a gibberellin inactivation enzyme, such as the gibberellin 2-oxidase gene. Such ribozyme-encoding DNA would generally be useful in inhibiting the deactivation of gibberellins. Alternatively, the RNA may encode a short interfering RNA sequence capable of activating the RNAi cellular process for degrading a target RNA species of interest, such as RNA coding a gibberellin deactivation enzyme.

RNAi can involve intron-spliced hairpin (ihpRNA) constructs (Smith, N. A., et al. (2000) Nature, 407:319-320), using 300-600 bp of the transcribed region of the target inserted in sense and antisense orientation flanking the intron of an ihpRNA vector such as pHELLSGATE (Wesley, S. V., et al. (2001) Plant J., 27:581-590.). Design of hammerhead ribozymes against target sequences, for example, GA2ox, may follow guidelines, for example Fritz, J. J., et al. (Methods (2002), 28:276-285). The ribozyme would be produced from synthetic oligonucleotides, annealed and inserted into an appropriate vector. It is preferable to use tissue-specific promoters for expression of antisense/RNAi/ribozymes in transgenic plants to avoid pleiotropic effects in other tissues. The promoters listed in the application are suitable. The constructs or RNAi fragments are introduced into the target species by routine methods in the art as described herein.

Nucleic acid sequences in accordance with the present invention may further comprise 5' signal sequences to direct expression of the expressed protein product.

Such signal sequences may also include protein targeting sequences which can direct an expressed protein to a particular location inside or outside of a host cell expressing such a nucleic acid sequence. Alternatively, the nucleic acid sequence may also comprise a 3' signal such as a polyadenylation signal or other regulatory signal.

Preparation of transgenic plants according to the present invention which have increased seed weight may therefore be prepared by modification of a plant cell to contain a nucleic acid sequence as described above which provides for expression of a nucleic acid sequence encoding an enzyme of gibberellin biosynthesis or an enzyme which renders gibberellins resistant to inactivation, or for expression of nucleic acid molecules to inhibit the expression of enzymes of gibberellin inactivation. Such nucleic acid sequences as herein defined can be introduced into plant cells by any suitable means. Expression of a nucleic acid includes overexpression above basal or endogenous levels.

Preferably, nucleic acid sequences of the present invention are introduced into plant cells by transformation using an appropriate vector, e.g. pMON57004 as shown in FIG. 1. Alternatively, a binary vector, for example a modified version of pGPTV-Kan (Becker et al Plant Mol. Biol. 20 1195-1197 (1992)) in which the β-glucuronidase reporter gene is replaced by the HMWGlu-GA20ox1 expression cassette. Such plasmids may be then introduced into *Agrobacterium tumefaciens* by electroporation and can then be transferred into the host cell via a vacuum filtration procedure. Alternatively, transformation may be achieved using a disarmed Ti-plasmid vector and carried by *Agrobacterium* by procedures known in the art, for example as described in EP-A-0116718 and EP-A-0270822. Where *Agrobacterium* is ineffective, the foreign DNA could be introduced directly into plant cells using an electrical discharge apparatus alone, such as for example in the transformation of monocotyledonous plants. Any other method that provides for the stable incorporation of the nucleic acid sequence within the nuclear DNA or mitochondrial DNA of any plant cell would also be suitable. This includes species of plant which are not yet capable of genetic transformation.

Preferably, nucleic acid sequences as described herein for introduction into host cells also contain a second chimeric gene (or "marker" gene) that enables a transformed plant containing the foreign DNA to be easily distinguished from other plants that do not contain the foreign DNA. Examples of such a marker gene include antibiotic resistance (Herrera-Estrella et al *EMBO J.* 2 987-995 (1983)), herbicide resistance (EP-A-0242246) and glucuronidase (GUS) expression (EP-A-0344029). Expression of the marker gene is preferably controlled by a second promoter which allows expression in cells at all stages of development so that the presence of the marker gene can be determined at all stages of regeneration of the plant.

A whole plant can be regenerated from a single transformed plant cell, and the invention therefore provides transgenic plants (or parts of them, such as propagating material, i.e. protoplasts, cells, calli, tissues, organs, seeds, embryos, ovules, zygotes, tubers, roots, etc.) including nucleic acid sequences as described above.

In the context of the present invention, it should be noted that the term "Genetically modified" should not be taken to be limited in referring to an organism as defined above containing in their germ line one or more genes from another species, although many such organisms will contain such a gene or genes, i.e. a "transgenic" plant. Rather, the term "genetically modified" refers more broadly to any organism whose germ line has been the subject of technical intervention, for example by recombinant DNA technology or chemical mutagenesis. So, for example, an organism in whose germ line an endogenous gene has been deleted, duplicated, activated or modified is a genetically modified organism for the purposes of this invention as much as an organism to whose germ line an exogenous DNA sequence has been added.

Screening of plant cells, tissue and plants for the presence of specific DNA sequences may be performed by Southern analysis as described in Sambrook et al (*Molecular Cloning: A Laboratory Manual*, Second edition (1989)). This screening may also be performed using the Polymerase Chain Reaction (PCR) by techniques well known in the art.

Transformation of plant cells includes separating transformed cells from those that have not been transformed. One convenient method for such separation or selection is to incorporate into the material to be inserted into the transformed cell a gene for a selection marker. As a result only those cells which have been successfully transformed will contain the marker gene. The translation product of the marker gene will then confer a phenotypic trait that will make selection possible. Usually, the phenotypic trait is the ability to survive in the presence of some chemical agent, such as an antibiotic, e.g. kanamycin, G418, paromomycin, etc, which is placed in a selection media. Some examples of genes that confer antibiotic resistance, include for example, those coding for neomycin phosphotransferase kanamycin resistance (Velten et al *EMBO J.* 3 2723-2730 (1984)), hygromycin resistance (van den Elzen et al *Plant Mol. Biol.* 5 299-392 (1985)), the kanamycin resistance (NPT II) gene derived from Tn5 (Bevan et al *Nature* 304 184-187 (1983); McBride et al *Plant Mol. Biol.* 14 (1990)) and chloramphenicol acetyltransferase. The PAT gene described in Thompson et al (*EMBO J.* 6 2519-2523 (1987)) may be used to confer herbicide resistance.

An example of a gene useful primarily as a screenable marker in tissue culture for identification of plant cells containing genetically engineered vectors is a gene that encodes an enzyme producing a chromogenic product. One example is the gene coding for production of β-glucuronidase (GUS). This enzyme is widely used and its preparation and use is described in Jefferson (*Plant Mol. Biol. Reporter* 5 387-405 (1987)).

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant using, for example, the *Agrobacterium* Ti-plasmid, those plant cells or plants transformed by the Ti-plasmid so that the enzyme is expressed, can be selected by an appropriate phenotypic marker. These phenotypic markers include, but are not limited to, antibiotic resistance. Other phenotypic markers are known in the art and may be used in this invention.

Positive clones are regenerated following procedures well-known in the art. Subsequently transformed plants are evaluated for the presence of the desired properties and/or the extent to which the desired properties are expressed. A first evaluation may include, for example, the level of bacterial/fungal resistance of the transformed plants, stable heritability of the desired properties, field trials and the like.

The methods of present invention extend to methods for the preparation of transgenic plants and the sexual and/or asexual progeny thereof, which have been transformed with a recombinant DNA sequence as defined herein. The regeneration of the plant can proceed by any known convenient method from suitable propagating material either prepared as described above or derived from such material.

The expression "asexual or sexual progeny of transgenic plants" includes by definition according to the invention all mutants and variants obtainable by means of known process, such as for example cell fusion or mutant selection and which still exhibit the characteristic properties of the initial transformed plant, together with all crossing and fusion products of the transformed plant material.

The methods of the invention also concern the proliferation material of transgenic plants. The proliferation material of transgenic plants is defined relative to the invention as any plant material that may be propagated sexually in vivo or in vitro. Particularly preferred within the scope of the present invention are protoplasts, cells, calli, tissues, organs, seeds, embryos, egg cells, zygotes, together with any other propagating material obtained from transgenic plants.

Gibberellin metabolism is the term used to describe the enzyme pathway for the biosynthesis in the cell of the active gibberellin molecules and for the regulation of the biosynthetic pathway through the activity of inhibitory or degradatory enzymes or other mechanisms, which includes the catabolism of gibberellins.

Manipulation of gibberellin content, preferably bioactive gibberellin content as described herein comprises the expression of a nucleic acid sequence encoding an enzyme of gibberellin metabolism (i.e. gibberellin biosynthesis or catabolism) or an enzyme which renders gibberellins resistant to inactivation, or the expression of nucleic acid molecules to inhibit the expression of enzymes of gibberellin inactivation. Expression includes overexpression above basal or endogenous levels. Preferably, the manipulation of gibberellin metabolism is caused by the expression of nucleic acid sequences as herein defined in the seeds of the plant, or by the ablation of the expression of genes that control inactivation of gibberellins in the seeds of the plant. The result of such manipulations is an increase in the level of gibberellin in the seed compared to normal levels of gibberellins in a control plant seed of the same species.

Gibberellin molecules known to occur as biologically active molecules in plant tissues, including seeds are $GA_1$, $GA_3$, $GA_4$ and $GA_7$. However, use of the term "gibberellins" also includes other bioactive gibberellins. In fact, the method of the invention relates to increasing abundance of bioactive GAs as a whole.

Overproduction of enzymes involved in gibberellin biosynthesis coded for by these genes referred to above can be achieved by expression including overexpression of the gene under a suitable promoter active in developing seeds as described above. Expression includes overexpression above basal or endogenous levels. For example, overexpression of the gene may comprise overproduction of the enzymes involved in gibberellin biosynthesis coded for by the gene with respect to basal or endogenous levels of expression.

Reduction or abolition of gene expression as described above can be achieved using antisense or sense suppression, RNAi or the identification of mutants with reduced expression. Reduction or abolition of enzyme activity can be achieved through the identification of mutagen-induced or existing lines with altered properties, for example by TILLING (McCallum C M, et al., Plant Physiol. 123:439-442; 2000).

Increasing GA concentration through manipulation of GA biosynthesis or turnover in during seed development according to the present invention leads to increased seed volume and weight. Weight-per-grain increases of at least 5%, suitably in the range of from 5% to 40%, preferably from 10% to 40%, most preferably from 20% to 30%, can be achieved, compared to plant seed from control plants grown under normal conditions which have not been subject to genetic modification. An increase in weight of at least 5% is statistically significant and represents a measurable and real improvement in crop yield.

As noted above an increase in the size of seed of a plant can be characterised by an increase in volume of the seed as well as by its weight. The present invention therefore also extends to a method of increasing the volume per unit plant seed, the method comprising preparing a transgenic plant in which gibberellin content has been manipulated in the seed of the plant.

According to a further aspect of the invention, there is provided the use of a nucleic acid sequence encoding an enzyme of gibberellin metabolism (i.e. gibberellin biosynthesis or catabolism) in the preparation of plant seed with an increased weight.

According to a further aspect of the invention, there is provided the use of a nucleic acid sequence encoding an enzyme which renders gibberellins resistant to inactivation in the preparation of plant seed with an increased weight.

According to a further aspect of the invention, there is provided the use of a nucleic acid sequence encoding a nucleic acid molecule which inhibits the expression of enzymes of gibberellin inactivation in the preparation of plant seed with an increased weight.

According to a further aspect of the invention, there is provided method of increasing the drought resistance of a plant seed, which comprises preparing a genetically modified plant in which gibberellin content has been manipulated in the seed of the plant, thereby increasing the weight of the plant seed.

By way of illustration and summary, the following scheme sets out a typical process by which genetically modified plant material, including whole plants, may be prepared according to a method of the present invention for increasing seed size. The process can be regarded as involving five steps:

(1) first isolating from a suitable source (or DNA library) or synthesising by means of known processes a DNA sequence encoding a protein exhibiting gibberellin enzyme activity, or a DNA sequence which upon expression yields a nucleic acid sequence capable of inhibiting expression of such enzymes;

(2) operably linking the said DNA sequence in a 5' to 3' direction to plant expression sequences as defined herein;

(3) transforming the construct of step (2) into plant material by means of known processes and expressing it therein;

(4) screening of the plant material treated according to step (3) for the presence of a DNA sequence encoding a protein exhibiting gibberellin synthetic activity or for a nucleic acid sequence having gibberellin inhibitory activity: and (5) optionally regenerating the plant material transformed according to step (3) to a whole plant.

Alternatively, genetically modified plants in which the gibberellin content has been increased in the seed of the plant through reduced inactivation, resulting in increased weight of plant seed, may be generated as follows:

(1) Identify a suitable source of DNA encoding an enzyme or enzymes involved in gibberellin biosynthesis, for example GA 2-oxidases (GA2ox);

(2) Identify the gene family members that encode the enzyme(s) which is/are expressed in the seeds of the plant, for example, by transcript analysis by Northern blotting, RT-PCR or microarrays;

(3) Design a single antisense RNA, RNAi or ribozyme construct that will target all the genes encoding enzymes involved in gibberellin biosynthesis which are expressed in the plant seed, if these genes have high sequence identity. Alternatively, design separate antisense RNA, RNAi or ribozyme constructs if sequence homology is lower;

(3a) For antisense RNA, amplify the whole cDNA or smaller fragments (>200 bp) by PCR and insert in an appropriate expression vector in reverse orientation to the promoter; or (3b) Design an intron-spliced hairpin (ihpRNA) construct; or (3c) Design a hammerhead ribozyme and insert into an appropriate vector;

(4) Antisense/RNAi/ribozyme constructs can be introduced into the target species by *Agrobacterium*-mediated transformation or microprojectile bombardment as appropriate, followed by assessment of effects on GA2ox expression and seed development.

Another example of an approach for identifying a suitable DNA source is to identify loss-of-function or reduced-function variants of the target genes using TILLING or other sequence variant detection methods. TILLING can identify sequence variants in the target gene(s) in natural or induced populations of crop species (McCallum, C. M., et al. (2000) Plant Physiol., 123:439-442; Comai, L., et al. (2004) Plant J., 37:778-786; Slade, A. J., et al. (2005) Nature Biotechnology, 23:75-81). A simplified protocol could be:

(1) Determine gene expression patterns (for example GA2ox) to identify target genes as above;

(2) Design sequence specific primers to amplify conserved exon-rich regions from genomic DNA (homoeologue-specific primers for allopolyploid species);

(3) Carry out TILLING method, involving PCR, heteroduplex annealing, cell cleavage and product detection, to identify sequence variants and confirm this by DNA sequencing; and (4) Back-cross to remove unwanted mutations and assess the effects.

A DNA sequence encoding a protein exhibiting gibberellin enzyme activity as used herein includes nucleic acid sequences encoding an enzyme of gibberellin metabolism, which may be gibberellin biosynthesis or gibberellin catabolism, or an enzyme which renders gibberellins resistant to inactivation. A DNA sequence encoding a nucleic acid molecule that is capable of inhibiting the expression of enzymes of gibberellin inactivation may be an antisense DNA sequence or short interfering RNA sequence capable of activating a process of RNAi in the plant cell leading to the inhibition of gene expression of the affected gene of gibberellin biosynthesis.

Alternatively, as described above, the genetically modified plant may be produced through the action of chemically induced mutagenesis of a subject plant or plant tissue, followed by screening to identify plants or plant tissue with the desired genetic characteristics.

In its broadest aspect, the invention can be described as a means of increasing yield of plant crop per unit area of the crop. Such methods of preparing transgenic plants having increased seed size offer several advantages, not least of which is an overall increase in yield. In addition, substantial advantages are associated with the greater storage capacity of increased seed size. These include seedling vigour, whereby larger seeds would nourish the growing seedling for a longer period before it becomes photosynthetically competent and self-sustaining. This would allow deeper planting and thus improve drought resistance.

Preferred features for the second and subsequent aspects of the invention are as for the first aspect mutatis mutandis.

The invention will now be further described by way of reference to the following Examples and Figures which are provided for the purposes of illustration only and are not to be construed as being limiting on the invention. Reference is made to a number of Figures in which:

FIG. 2 shows photographs of $T_3$ seeds from DE45 transgenic lines ($T_2$) and a null (azygous) line.

FIG. 3 (SEQ ID No: 1) shows the nucleotide sequence of the promoter of the High Molecular Weight Glutenin-1-D1 gene from wheat (*Triticum aestivum* cv Cheyenne; EMBL accession AJ301618; Lamacchia, et al., 2001) with added PacI and StuI restriction sites at the 5' and 3' ends, respectively.

FIG. 4 (SEQ ID No: 2) shows the nucleotide sequence of the coding region of the gibberellin 20-oxidase-1 gene from *Arabidopsis thaliana* (accession Landsberg erecta); EMBL accession X83379; Phillips, et al., 1995) with added XhoI and SacI sites at the 5' and 3' ends, respectively.

FIG. 5 (SEQ ID No: 3) shows the amino acid sequence of the gibberellin 20-oxidase isozyme-1 from *Arabidopsis thaliana* as encoded by FIG. 4 (sequence 2).

FIG. 6 (SEQ ID No: 4) shows the nucleotide sequence of the gibberellin 3β-hydroxylase-1 gene from *Arabidopsis* (AtGA3ox1, Genbank No. L37126, Chiang H H et al., Plant Cell 7: 195-201; 1995).

FIG. 7 (SEQ ID No: 6) shows the protein sequence of the gibberellin 3β-hydroxylase-1 gene from *Arabidopsis* (AtGA3ox1, Genbank No. L37126, Chiang H H et al., Plant Cell 7: 195-201; 1995).

FIG. 8 (SEQ ID No: 5) shows the nucleotide sequence of the gibberellin 1,2-desaturase from *Gibberella fujikuroi* which renders GAs resistant to inactivation (GAdes; Genbank No. AJ417493, Tudzynski B, et al., J. Biol. Chem. 278: 28635-28643; 2003).

FIG. 9 (SEQ ID No: 7) shows the protein sequence of the gibberellin 1,2-desaturase from *Gibberella fujikuroi* which renders GAs resistant to inactivation (Sequences 5 & 6: GAdes; Genbank No. AJ417493, Tudzynski B, et al., J. Biol. Chem. 278:28635-28643; 2003).

FIG. 10 (SEQ ID No: 8) shows the nucleotide sequence of the gibberellin inactivation enzyme from wheat, gibberellin 2β-hydroxylase-2 (GA 2-oxidase-2; TaGA2ox2; Phillips A L., et al., unpublished).

FIG. 11 (SEQ ID No: 9) shows the protein sequence of the gibberellin inactivation enzyme from wheat, gibberellin 2β-hydroxylase-2 (GA 2-oxidase-2; TaGA2ox2; Phillips A L., et al, unpublished).

Figure 12:
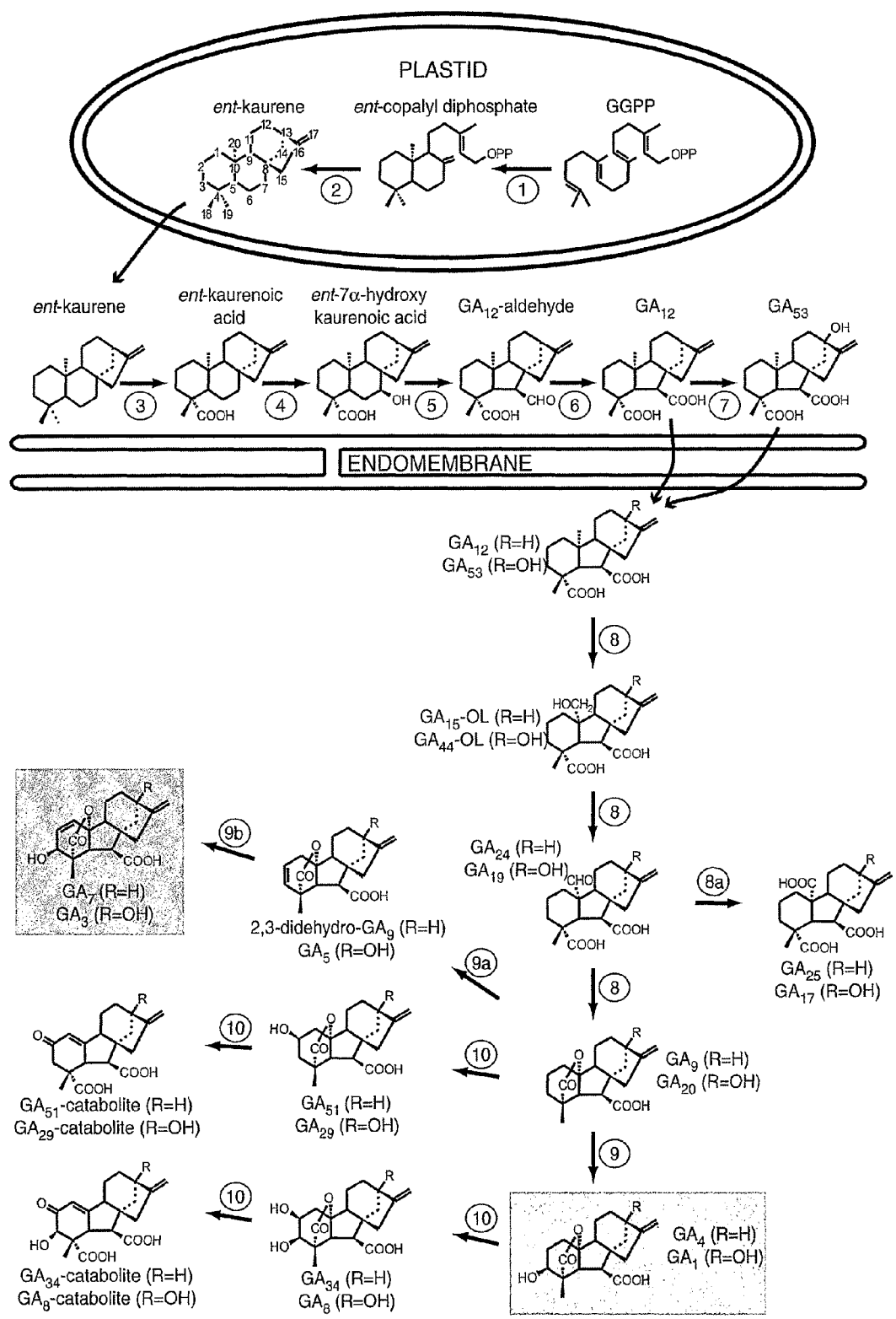

FIG. 12 shows the main pathways of gibberellin (GA) biosynthesis in plants. The labelled enzymes are: (1) ent-copalyldiphosphate synthase, (2) ent-kaurene synthase, (3) ent-kaurene oxidase, (4,5,6), ent-kaurenoic acid oxidase, (7) GA 13-hydroxylase, (8) GA 20-oxidase, (9,a,b) GA 3β-hydroxylase, (10) GA 2-oxidase.

EXAMPLE 1

Construction of an HMWGlu::AtGA20ox1 Expression Cassette

Figure 1:
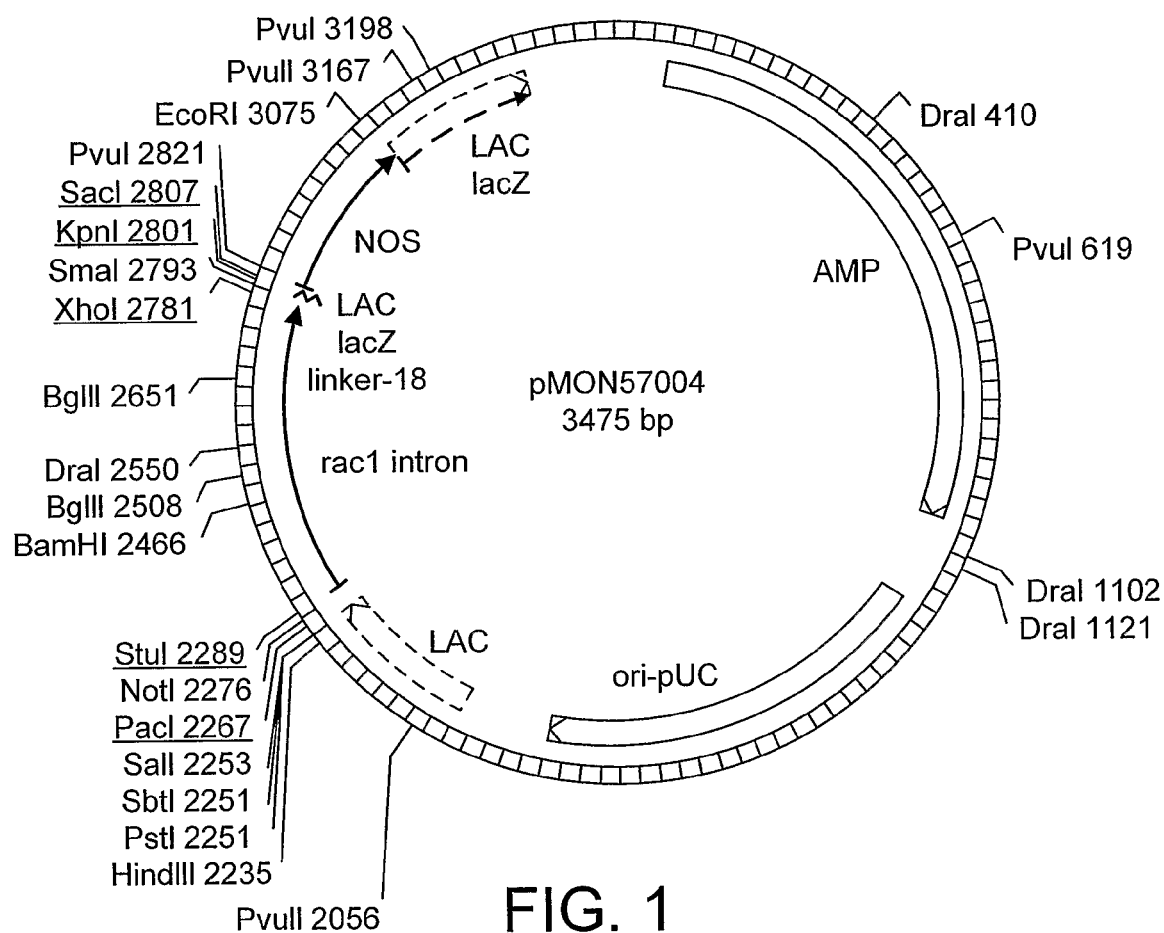
FIG. 1 shows a map of plasmid pMON57004. Plasmid pMON57004 used as the basis for construct pDE45.

The promoter of the High Molecular Weight Glutenin-1-D1 gene from wheat (*Triticum aestivum* cv Cheyenne; EMBL accession AJ301618; Lamacchia, et al., 2001) was amplified by PCR from plasmid pHMWGlu-1-D1 using the primers HMW-L (5'-AAATTAATTAAAAATATGCAACAT-AATTTCC-3') (SEQ ID No: 10) and HMW-R (5'-AAAAG-GCCTGGTGGACTATCAGTAATTGA-3') (SEQ ID No: 11) to create PacI and StuI restriction sites at the 5' and 3' ends, respectively. This HMWGlu-1-D1 promoter fragment (Sequence 1) was inserted into the PacI-StuI sites of plasmid pMON57004 (FIG. 1) upstream of the rice Actin-1 intron to yield plasmid pMON57004-HMWG. The coding region of the gibberellin 20-oxidase-1 gene from *Arabidopsis thaliana* (accession Landsberg erecta); EMBL accession X83379; Phillips, et al., 1995) was PCR-amplified from plasmid pAtGA20ox1 using primers 20ox1-L (5'-AAACTC-GAGATGGCCGTAAGTTTCGTAAC-3') (SEQ ID No: 12) and 20ox1-R (5'-AAAGAGCTCTTAGATGGGTTTGGT-GAGCC-3') (SEQ ID No: 13) to create XhoI and SacI sites at the 5' and 3' ends, respectively. This AtGA20ox1 fragment (Sequence 2), encoding gibberellin 20-oxidase isozyme 1 (Sequence 3) was inserted into the XhoI-SacI sites of pMON57004-HMWG, between the rice Actin-1 intron and the NOS terminator.

EXAMPLE 2

Wheat Transformation

Bread wheat (*Triticum aestivum* cv Cadenza) was transformed with plasmid pDE45 by particle bombardment of immature embryo tissue. Wheat plants were grown, 5 per 20 cm diameter pot, in an environmentally-controlled room with air temperatures of 18° C./15° C. (day/night), a relative humidity of 50-70% under ca. 350 µmol/m$^2$/s irradiance with a photoperiod of 16 hours. Immature scutella isolated from seeds at approximately 14-16 days post anthesis were co-transformed using the PDS1000/He micro-projectile bombardment device (BioRad, Hemel Hempstead, UK) with pDE45 and pAHC25 (containing the selectable marker gene bar; Christensen & Quail P 1996) at a 1:1 molar ratio. Plants were recovered via in vitro tissue culture using Bialaphos selection following protocols developed by Barcelo and Lazzeri (1995) and modified by Pastori et al. (2001), Rasco-Gaunt et al. (2001) and Sparks & Jones (2004). Four transgenic T$_1$ lines (T45-2 through T45-5) that survived selection were transferred to soil and grown to maturity in an environmentally-contained glasshouse to produce T$_2$ seed. Twenty (20) T$_2$ seeds of each line were re-sown and leaf material tested by PCR to identify segregants containing the DE45 transgene. All lines were grown through to maturity and T$_3$ grain collected. T$_3$ seedlings were produced and tested for the presence of the DE45 construct by PCR in order to identify lines homozygous for the transgene.

EXAMPLE 3

Seed Analysis

Seeds of the four primary transgenic lines, T45-2 through T45-5, had larger seed than control (non-transformed) lines. Average seed weights (Table 1) indicated that plants containing pDE45 had seeds that were between 10% and 40% heavier than the control.

Larger seeds were also observed on T$_2$ plants that tested positive for the DE45 transgene—see FIG. 2. Mean Grain weights of these T$_3$ seeds were also increased by 19-32% over seeds from null (azygous, non-transgenic) lines (Table 2).

TABLE 1

| Grain weights and yields of primary transgenic (T$_1$) lines (T$_2$ seeds) | | | | |
|---|---|---|---|---|
| Plant | Construct | Mean grain no./Ear | Mean Grain weight in g | Mean grain weight g/plant |
| T45.2 | DE45 | 60.08 | 0.049 | 17.79 |
| T45.3 | DE45 | 63.22 | 0.056 | 21.09 |
| T45.4 | DE45 | 54.38 | 0.063 | 20.49 |
| T45.5 | DE45 | 56.76 | 0.061 | 20.74 |
| Control | n/a | 58.45 | 0.044 | 15.56 |

| Grain weights from T$_2$ plants (T$_3$ seeds) and Null (azygous) lines | | | | | |
|---|---|---|---|---|---|
| Line | 45.2 | 45.3 | 45.4 | 45.5 | Nulls |
| Mean grain | 61.6 | 60 | 61.6 | 56.8 | 51.2 |
| weights | 62.4 | 58.4 | 67.2 | 66 | 53 |
| of sub-lines | 64.4 | 58.4 | 58.4 | 66.8 | 50 |
| (g/grain) | 50.8 | 66.8 | 66 | 58.8 | 38.8 |
|  | 50.4 | 55.6 | 69.2 | 60.4 | 44 |
|  | 66.4 | 58 | 60 | 73.2 | 46.8 |

-continued

Grain weights from T₂ plants (T₃ seeds) and Null (azygous) lines

|  |  |  |  |  |  |
|---|---|---|---|---|---|
|  | 60.8 | 58.8 | 68.8 | 61.6 | 47.2 |
|  | 52.8 | 58.8 | 75.6 | 63.6 | 47.6 |
|  | 50.4 | 59.6 | 61.2 | 58.8 | 54.8 |
|  | 57.6 | 58.8 | 62.8 | 55.6 | 48.8 |
|  | 59.6 | 60.4 | 58.8 | 49.6 | 52.4 |
|  | 56 |  | 59.2 | 56.8 | 51.2 |
|  |  |  |  | 74.8 | 48.4 |
|  |  |  |  | 70.0 | 50.8 |
|  |  |  |  |  | 42.8 |
|  |  |  |  |  | 45.2 |
|  |  |  |  |  | 51.2 |
|  |  |  |  |  | 46.8 |
|  |  |  |  |  | 50 |
| Means (g/grain) | 57.8 | 59.4 | 64.1 | 62.3 | 48.5 |
| % increase over Null |  | 19 | 23 | 32 | 29 |

EXAMPLE 4

Growth of a Subsequent Generation ($T_3$) of Transgenic Wheat Plants and Analysis of the Seed ($T_4$ seeds)

Three independent transgenic ($T_3$) lines, homozygous for the HMWGlu-GA20ox cassette, together with Control (non-transgenic wheat cv. Cadenza) were grown, 15 plants per line, in controlled environment. Plants were grown under a 16 hr day at 700 micromole per meter squared per second of white light, at a temperature of 20° C. (day), 18° C. (night) and 80% relative humidity. A randomized block pattern was used to avoid position effects within the cabinet. At the boot stage, each plant was reduced to three main tillers; after seed filling and maturation, plants were allowed to desiccate completely and the ears harvested. Two seeds were harvested from each of two central spikelets of each ear and the four seeds weighed individually. All harvested seed from each line was then pooled and the volume of 50 seeds measured by ethanol displacement using a 10 ml glass density bottle (Table 3).

TABLE 3

Grain weights and yields of transgenic ($T_3$) lines ($T_4$ seeds)

|  | Control | Line 45.2.3 | Line 45.3.11 | Line 45.5.8 |
|---|---|---|---|---|
| Mean seed vol (ul) | 39.1 | 46.9 | 49.6 | 45.7 |
| Increase over control |  | 20% | 27% | 17% |
| Mean seed weight (mg) | 51.4 | 59.8 | 60.9 | 57.2 |
| Increase over control |  | 16% | 19% | 11% |

REFERENCES

Barcelo P, & Lazzeri P. (1995). In *Methods in Molecular Biology: Plant Gene Transfer and Expression Protocols*, p. 113-123. Eds H. Jones. Humana Press: Totowa N.J.

Christensen A H, & Quail P H. (1996). *Transgenic Research*. 5:213-218.

Lamacchia et al., (2001) *J. Exp. Bot.* 52:243-250.

Pastori et al., (2001) *Journal of Experimental Botany*. 52:857-863.

Phillips et al., (1995) *Plant Physiol*. 108:1049-1057.

Rasco-Gaunt et al., (2001) *Journal of Experimental Botany*. 52:865-874.

Sparks C A, & Jones H D. (2004). Transformation of wheat by biolistics, In *Transgenic Crops of the World—Essential Protocols*. Ed I. S. Curtis. Kluwer: Dordrecht: Netherlands.

The invention claimed is:

1. A method of increasing the weight of plant seed, the method comprising preparing a genetically modified plant in which the gibberellin content has been increased in the seed of the plant.

2. The method as claimed in claim 1, in which the plant is monocotyledonous.

3. The method as claimed 2, in which monocotyledonous plant is selected from the group consisting of wheat, maize, rye, rice, oat, barley, sorghum and millet.

4. The method as claimed in claim 1, in which the plant is dicotyledenous.

5. The method as claimed in claim 4, in which the dicotyledonous plant is selected from the group consisting of soybean, canola, and sunflower.

6. A method as claimed in claim 1, in which the gibberellin content has been increased by (i) expression of a nucleic acid sequence encoding an enzyme of gibberellin biosynthesis or of an enzyme which renders gibberellins resistant to inactivation, (ii) by expression of a nucleic acid molecule to inhibit the expression of enzymes of gibberellin inactivation, or (iii) by mutagenesis of the plant.

7. The method as claimed in claim 6, in which the gibberellin content has been increased by expression of a nucleic acid sequence encoding an enzyme of gibberellin metabolism comprising a nucleic acid sequence as shown in SEQ ID NO:2 or SEQ ID NO:4, or its complementary strand or a homologous sequence thereto.

8. The method as claimed in claim 6, in which the enzyme of gibberellin biosynthesis is gibberellin 20-oxidase (GA20ox) or gibberellin 3β-hydroxylase (GA 3-oxidase).

9. The method as claimed in claim 6, in which the gibberellin content has been increased by expression of a nucleic acid sequence encoding an enzyme which renders gibberellins resistant to inactivation comprising a nucleic acid sequence as shown in SEQ ID NO:5.

10. The method as claimed in claim 6, in which the enzyme that renders gibberellins resistant to inactivation is gibberellin 1,2-desaturase (GAdes).

11. The method as claimed in claim 6, in which the gibberellin content has been increased by expression of a nucleic acid molecule that inhibits the expression of gibberellin-2β-hydroxylase (GA 2-oxidase).

12. The method as claimed in claim 1, in which the increase in seed weight is of at least 5%.

13. The method as claimed in claim 12, in which the increase in seed weight is in the range of from 5% to 40%.

14. A plant seed in which the weight has been increased according to the method of claim 1.

15. A genetically modified plant comprising the plant seed of claim 14.

16. A method of increasing the volume per unit plant seed, the method comprising preparing a transgenic plant in which gibberellin content has been increased in the seed of the plant.

17. A method for the preparation of plant seed with an increased weight, said method comprising genetically modifying a plant with a nucleic acid sequence encoding an enzyme of gibberellin metabolism and expressing said enzyme, thereby increasing said plant's gibberellin metabolism and increasing the weight of the seed produced by said plant.

18. A method for the preparation of plant seed with an increased weight, said method comprising genetically modifying a plant with a nucleic acid sequence encoding an enzyme which renders gibberellins resistant to inactivation and expressing said enzyme, thereby rendering said plant's gibberellins resistant to inactivation and increasing the weight of the seed produced by said plant.

19. A method for the preparation of plant seed with an increased weight, said method comprising genetically modifying a plant with a nucleic acid sequence encoding a nucleic acid molecule which inhibits the expression of enzymes of gibberellin inactivation and expressing said nucleic acid molecule, thereby inhibiting said plant's expression of enzymes of gibberellin inactivation and increasing the weight of the seed produced by said plant.

20. A genetically modified plant comprising plant seed having an increased gibberellin content and an increased weight.

21. A genetically modified plant seed with an increased weight comprising an increased gibberellin content.

* * * * *